(12) United States Patent
Hiraga et al.

(10) Patent No.: US 6,790,836 B2
(45) Date of Patent: Sep. 14, 2004

(54) PROCESS FOR PREPARING INDOLOPYRROLOCARBAZOLE DERIVATIVES, INTERMEDIATES THEREFOR, AND PREPARATION PROCESS OF THE INTERMEDIATES

(75) Inventors: Shouichi Hiraga, Okazaki (JP); Masashi Kawasaki, Okazaki (JP); Atsushi Akao, Okazaki (JP); Asayuki Kamatani, Okazaki (JP); Masayuki Hagiwara, Okazaki (JP); Toshiaki Mase, Okazaki (JP); Fumio Nakano, Okazaki (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 10 days.

(21) Appl. No.: 10/203,088
(22) PCT Filed: Feb. 22, 2001
(86) PCT No.: PCT/JP01/01289
§ 371 (c)(1),
(2), (4) Date: Aug. 6, 2002
(87) PCT Pub. No.: WO01/62769
PCT Pub. Date: Aug. 30, 2001

(65) Prior Publication Data
US 2003/0060621 A1 Mar. 27, 2003

(30) Foreign Application Priority Data
Feb. 24, 2000 (JP) .................................... 2000-048140

(51) Int. Cl.[7] ................... A61K 31/70; C07H 19/00; C07C 241/00
(52) U.S. Cl. .................. 514/43; 536/22.1; 564/107
(58) Field of Search .................. 514/43; 536/22.1, 536/17.7, 18.7, 18.5; 564/107

(56) References Cited
U.S. PATENT DOCUMENTS
5,591,842 A    1/1997 Kojiri et al.
(List continued on next page.)
FOREIGN PATENT DOCUMENTS
EP         0 545 195 A1    6/1993
(List continued on next page.)
OTHER PUBLICATIONS
Ohkubo et al Bioorganic & Medicinal Chemistry Letters
(List continued on next page.)

*Primary Examiner*—Elli Peselev
(74) *Attorney, Agent, or Firm*—Nixon & Vanderhye P.C.

(57) ABSTRACT

A process for preparing indolopyrrolocarbazole derivatives [I] by trating a compound [V] with a base in an inert solvent to prepare a compound [IV], reacting the compound [IV] with a compound [III]to prepare a compound [II], and A process for preparing indolopyrrolocarbazole derivatives [I] by trating a compound [V] with a base in an inert solvent to prepare a compound [IV], reacting the compound [IV] with a compound [III]to prepare a compound [II], and deblocking the compound [II]; intermediates [II], [III] and [IV]; and a process for preparing compounds [III]: [wherein $Y^1$ is hydrogen, $C_{1-4}$ alkyl, phenyl, benzyloxymethyl, or aralkyl; $R^1$, $R^2$, $R^3$, $R^4$, $R^5$, and $R^6$ are each independently a hydroxyl-protecting group; $R^7$ and $R^8$ are each independently hydrogen or a hydroxyl-protecting group; and X is an acid molecule]. The above process is a safe and easy industrial process for preparing indolopyrrolocarbazole derivatives [1] useful as antitumor agents.

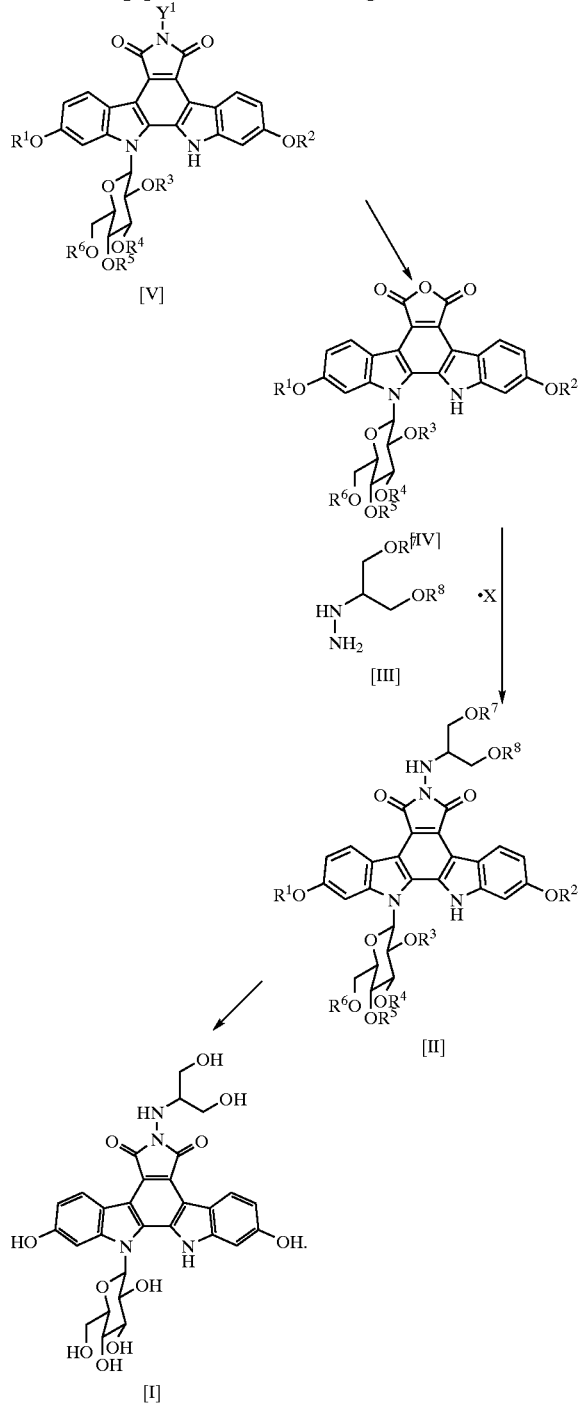

31 Claims, No Drawings

U.S. PATENT DOCUMENTS

| | | |
|---|---|---|
| 5,668,271 A | 9/1997 | Kojiri et al. |
| 5,804,564 A | 9/1998 | Kojiri et al. |
| 5,922,860 A | 7/1999 | Kojiri et al. |

FOREIGN PATENT DOCUMENTS

| | | |
|---|---|---|
| JP | 10-245390 | 9/1998 |
| WO | WO 95/30682 | 11/1995 |
| WO | WO 96/04293 | 2/1996 |
| WO | WO 97/09339 | 3/1997 |
| WO | WO 02/48166 A1 | 6/2002 |

OTHER PUBLICATIONS (2000), 10(5), 419–422, 2000, XP004202429 Synthesis and biological activities of NB–506 analogues modified at the glucose group.

Ohkubo et al, "Synthesis and Biological Activities of NB–506 Analogues: Effects of the Positions of two Hydroxyl Groups at the Indole Rings", Bioorganic & Medicinal Chemistry Letters 9 (1999) 3307–3312.

Ogilivie et al, "Synthesis of a Purine Acyclonucleoside Series Having Pronounced Antiviral Activity. the Glyceropurines", Can. J. Chem. 62, 241 (1984).

Csuk et al, "Preparation of Novel Difluorocyclopropane Nucleosides", Tetrahedron 55 (1999) 739–750.

Ghali et al, "A High–Yielding Synthesis of Monoalkylhydrazines", J. Org. Chem. 1981, 46, 5413–5414.

Harnden et al, Analogues of the Antiviral Acyclonucleoside 9–(4–Hydroxy–3–...), J. Chem. Soc. Perkin Trans. 1 1988, pp. 2757–2765.

PROCESS FOR PREPARING INDOLOPYRROLOCARBAZOLE DERIVATIVES, INTERMEDIATES THEREFOR, AND PREPARATION PROCESS OF THE INTERMEDIATES

This application is the US national phase of international application PCT/JP01/01289 filed 22 Feb. 2001 which designated the U.S.

TECHNICAL FIELD

This invention is a useful invention in the field of medicine. More detailedly, this invention relates to an industrially suitable process for preparation of a useful compound in the field of medicine, and novel preparation intermediates necessary for the preparation process and processes for preparation of the intermediates.

BACKGROUND ART

An indolopyrrolocarbazole derivative prepared by the preparation process of the invention and represented by the formula [I]:

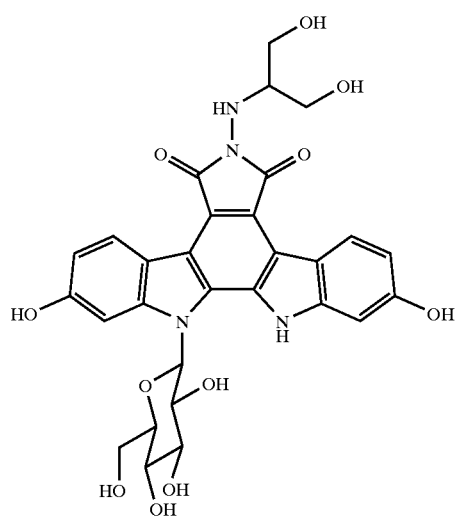

is a compound which has a carcinostatic activity and is now under clinical tests (Mitsuru Ohkubo et al., Bioorganic & Medicinal Chemistry Letters, volume 9, pages 3307–3312 (1999).

As to a process for preparation of the compound, there is a disclosure in WO95/30682.

The object of the invention lies in obviating undesirable points as an industrial preparation process from the process disclosed in WO95/30682. Namely, the object of the invention lies in deleting the steps shown below where highly physiologically active compounds are handled (Preparation steps of Compounds [b] and [c]), in the preparation process disclosed in WO95/30682.

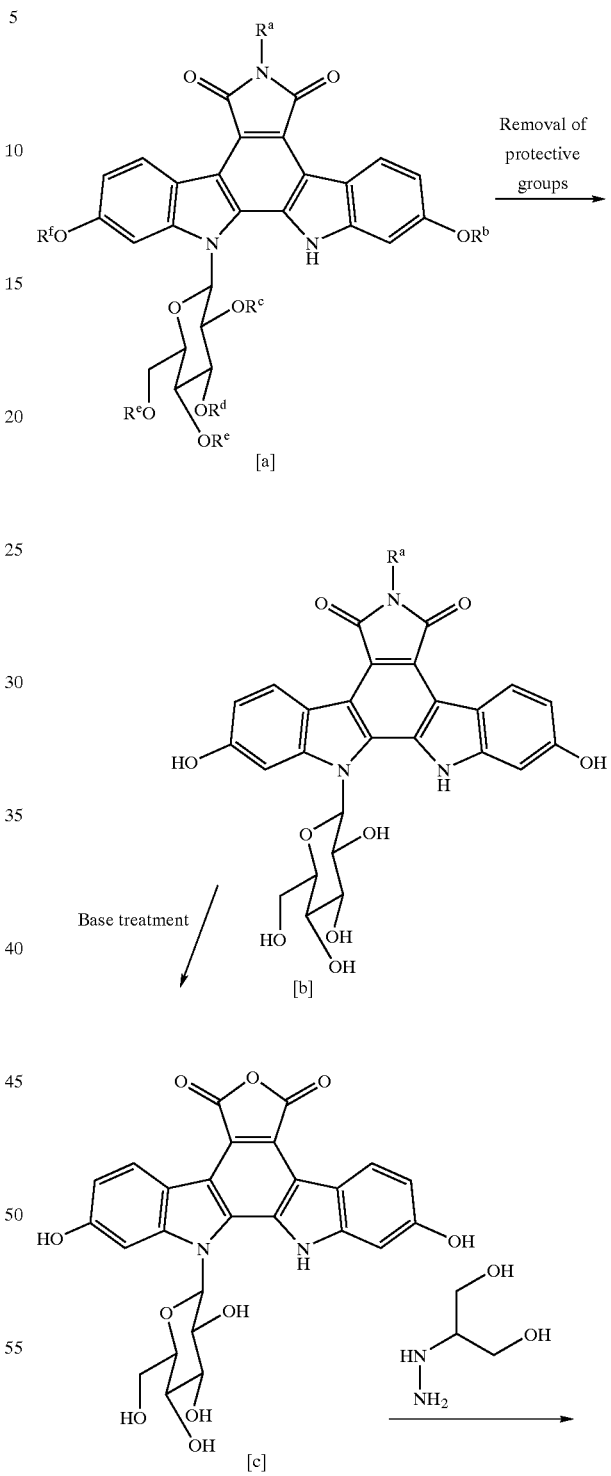

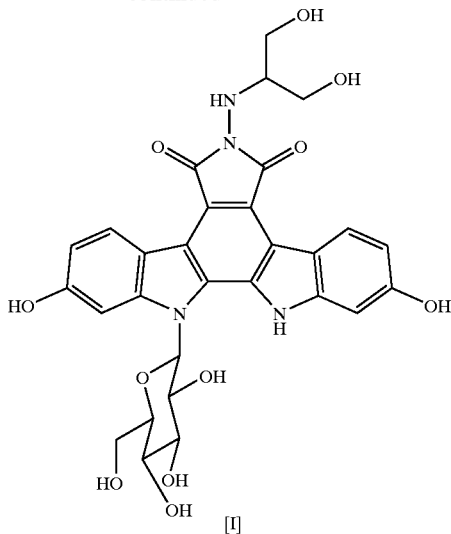

[I]

In the above, $R^a$ represents a hydrogen atom, a lower alkyl group, a benzyloxymethyl group or an aralkyl group, and $R^b$, $R^c$, $R^d$, $R^e$ and $R^f$ each represent a protective group of a hydroxyl group such as, for example, a benzyl group, a tolyl group, a p-methoxybenzyl group or a benzyloxymethyl group.

DISCLOSURE OF INVENTION

The present inventors have made sequential research into a process for preparation of the indolopyrrolocarbazole derivative [I], and as a result, they found the present preparation process of the indolopyrrolocarbazole derivative [I] which is excellent as an industrial process in the point that the step handling a highly physiologically active compound can be made to be only the final step, and completed the invention. Further, they also found that the respective preparation intermediates used in the preparation process of the indolopyrrolocarbazole derivative [I] of the invention are novel compounds.

Namely, the invention relates to the matters described in the following items (1) to (36).

(1) A process for preparation of an indolopyrrolocarbazole derivative represented by the formula [I]

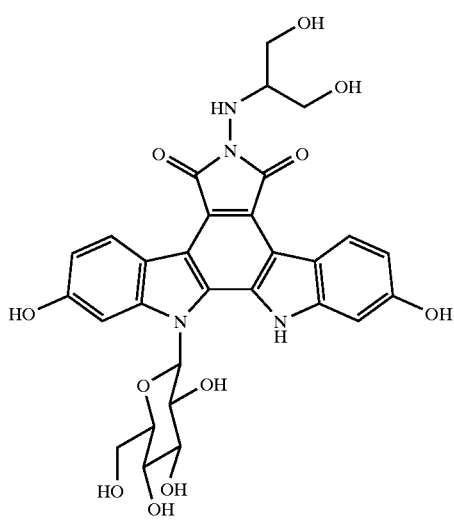

[I]

which comprises removing the protective groups of a compound represented by the general formula [II]:

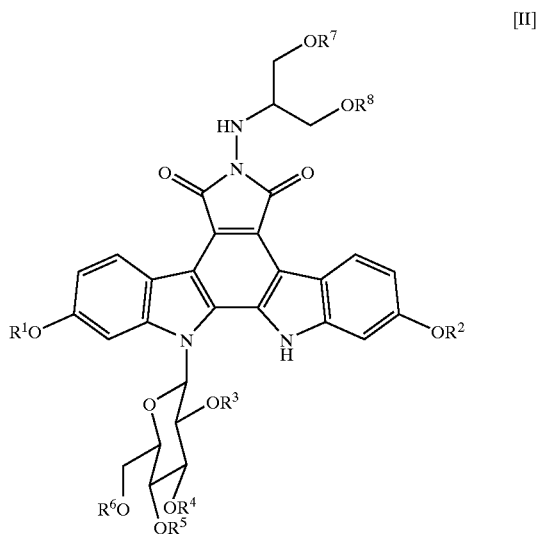

[II]

wherein $R^1$, $R^2$, $R^3$, $R^4$, $R^5$ and $R^6$ may be the same or different and each represent a protective group of a hydroxyl group, and $R^7$ and $R^8$ may be the same or different and each represent a hydrogen atom or a protective group of a hydroxyl group.

(2) The process according to item (1) wherein $R^1$, $R^2$, $R^3$, $R^4$, $R^5$, $R^6$, $R^7$ and $R^8$ are benzyl groups.

(3) The process according to item (1) wherein $R^1$, $R^2$, $R^3$, $R^4$, $R^5$ and $R^6$ are benzyl groups and $R^7$ and $R^8$ are hydrogen atoms.

(4) The process according to item (1) wherein the compound represented by the general formula [II] is obtained by reacting a compound represented by the general formula [IV]:

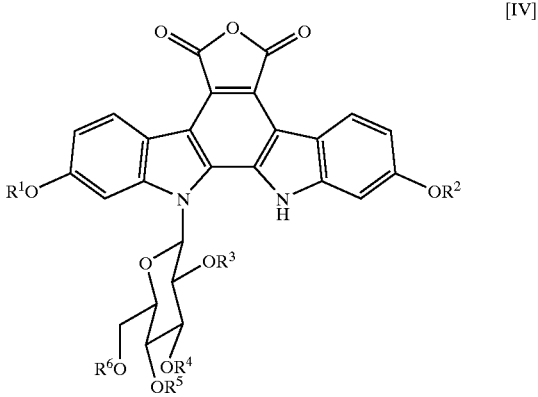

[IV]

wherein $R^1$, $R^2$, $R^3$, $R^4$, $R^5$ and $R^6$ may be the same or different and each represent a protective group of a hydroxyl group, with a hydrazinediol derivative acid addition salt represented by the general formula [III]:

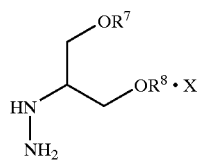

wherein X represents an acid molecule, and $R^7$ and $R^8$ may be the same or different and each represent a hydrogen atom or a protective group of a hydroxyl group, in the presence of an acid-capturing agent.

(5) The process according to item (4) wherein $R^1$, $R^2$, $R^3$, $R^4$, $R^5$, $R^6$, $R^7$ and $R^8$ are benzyl groups.

(6) The process according to item (4) wherein $R^1$, $R^2$, $R^3$, $R^4$, $R^5$ and $R^6$ are benzyl groups and $R^7$ and $R^8$ are hydrogen atoms.

(7) The process according to item (4) wherein X is oxalic acid.

(8) The process according to item (4) wherein the compound represented by the general formula [IV] is obtained by treating a compound represented by the general formula [V]:

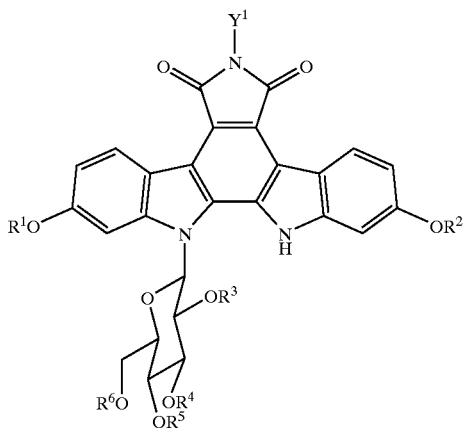

wherein $Y^1$ represents a hydrogen atom, an alkyl group having 1 to 4 carbon atoms, a phenyl group, a benzyloxymethyl group or an aralkyl group, and $R^1$, $R^2$, $R^3$, $R^4$, $R^5$ and $R^6$ may be the same or different and each represent a protective group of a hydroxyl group, with a base in an inert solvent.

(9) The process according to item (8) wherein $Y^1$ is a methyl group.

(10) The process according to item (8) wherein $R^1$, $R^2$, $R^3$, $R^4$, $R^5$ and $R^6$ are benzyl groups.

(11) A compound represented by the general formula [IV]:

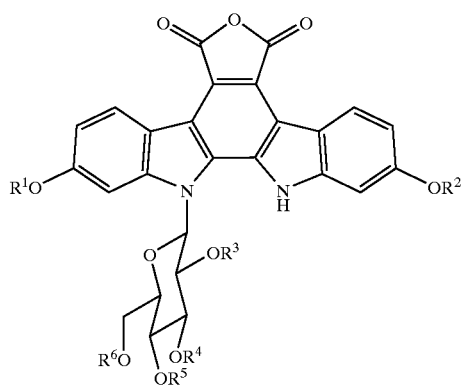

wherein $R^1$, $R^2$, $R^3$, $R^4$, $R^5$ and $R^6$ may be the same or different and each represent a protective group of a hydroxyl group.

(12) The compound according to item (11) wherein $R^1$, $R^2$, $R^3$, $R^4$, $R^5$ and $R^6$ are benzyl groups.

(13) A hydrazinediol derivative acid addition salt represented by the general formula [III]:

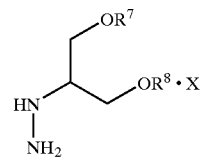

wherein X represents an acid molecule, and $R^7$ and $R^8$ may be the same or different and each represent a hydrogen atom or a protective group of a hydroxyl group.

(14) The compound according to item (13) wherein $R^7$ and $R^8$ are benzyl groups.

(15) The compound according to item (13) wherein $R^7$ and $R^8$ are hydrogen atoms.

(16) The compound according to item (13) wherein X is oxalic acid.

(17) A hydrazinediol derivative represented by the general formula [III-a]:

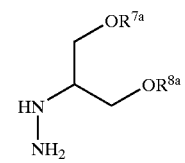

wherein $R^{7a}$ and $R^{8a}$ may be the same or different and each represent a protective group of a hydroxyl group.

(18) The compound according to item (17) wherein $R^{7a}$ and $R^{8a}$ are benzyl groups.

(19) A process for preparation of a hydrazinediol derivative acid addition salt represented by the general formula [III]:

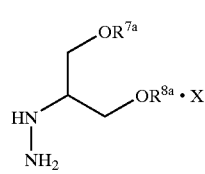

wherein $R^{7a}$ and $R^{8a}$ maybe the same or different and each represent a protective group of a hydroxyl group, and X represents an acid molecule, which comprises reacting a hydrazinediol derivative represented by the general formula [III-a]:

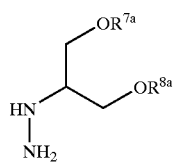

[III-a]

wherein $R^{7a}$ and $R^{8a}$ are as defined above, with an acid.

(20) The process according to item (19) wherein $R^{7a}$ and $R^{8a}$ are benzyl groups.

(21) The process according to item (19) wherein the hydrazinediol derivative represented by the general formula [III-a] is obtained by eliminating the protective group of the amino group of a hydrazinediol derivative represented by the general formula [III-b]:

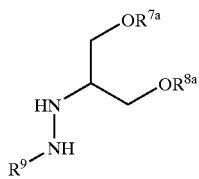

[III-b]

wherein $R^{7a}$ and $R^{8a}$ may be the same or different and each represent a protective group of a hydroxyl group.

(22) The process according to item (21) wherein $R^{7a}$ and $R^{8a}$ are benzyl groups and $R^9$ is a t-butoxycarbonyl group.

(23) The process according to item (21) wherein the hydrazinediol derivative represented by the general formula [III-b] is obtained by reducing a hydrazone derivative represented by the general formula [III-c]:

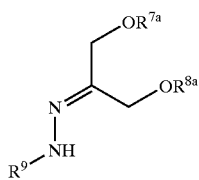

[III-c]

wherein $R^{7a}$ and $R^{8a}$ may be the same or different and each represent a protective group of a hydroxyl group, and $R^9$ represents a protective group of an amino group.

(24) The process according to item (23) wherein $R^{7a}$ and $R^{8a}$ are benzyl groups and $R^9$ is a t-butoxycarbonyl group.

(25) The process according to item (23) wherein the hydrazone derivative represented by the general formula [III-c] is obtained by reacting a dihydroxyacetone derivative represented by the general formula [III-e]:

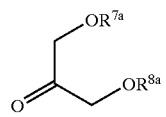

[III-e]

wherein $R^{7a}$ and $R^{8a}$ may be the same or different and each represent a protective group of a hydroxyl group, with a hydrazine derivative represented by the general formula [III-d]:

[III-d]

wherein $R^9$ represents a protective group of an amino group, in a mixed solvent.

(26) The process according to item (25) wherein $R^{7a}$ and $R^{8a}$ are benzyl groups and $R^9$ is a t-butoxycarbonyl group.

(27) The process according to item (25) wherein the dihydroxyacetone derivative represented by the general formula [III-e] is obtained by reacting a propanetriol derivative represented by the general formula [III-f]:

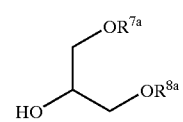

[III-f]

wherein $R^{7a}$ and $R^{8a}$ may be the same or different and each represent a protective group of a hydroxyl group, with a hypochlorite in an inert solvent in the presence of a catalyst and a buffer.

(28) The process according to item (27) wherein $R^{7a}$ and $R^{8a}$ are benzyl groups.

(29) A compound represented by the general formula [II]:

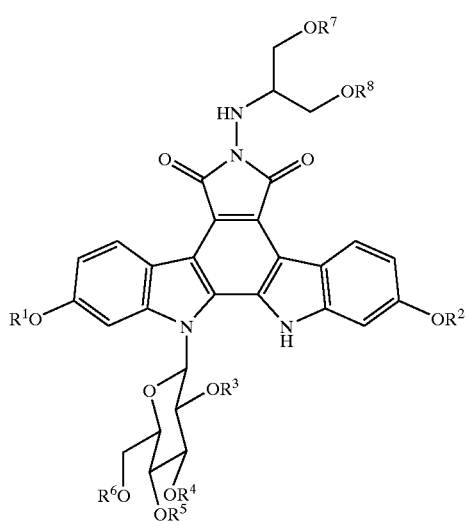

[II]

wherein, $R^1$, $R^2$, $R^3$, $R^4$, $R^5$ and $R^6$ may be the same or different and each represent a protective group of a hydroxyl group, and $R^7$ and $R^8$ may be the same or different and each represent a hydrogen atom or a protective group of a hydroxyl group.

(30) The compound according to item (29) wherein $R^1$, $R^2$, $R^3$, $R^4$, $R^5$, $R^6$, $R^7$ and $R^8$ are benzyl groups.

(31) The compound according to item (29) wherein $R^1$, $R^2$, $R^3$, $R^4$, $R^5$ and $R^6$ are benzyl groups, and $R^7$ and $R^8$ are hydrogen atoms.

(32) A hydrazinediol derivative represented by the general formula [III-b]:

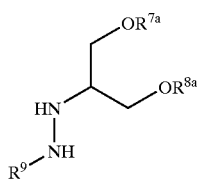

[III-b]

wherein $R^{7a}$ and $R^{8a}$ each represent a protective group of a hydroxyl group and $R^9$ represents a protective group of an amino group, or a salt thereof.

(33) The compound according to item (32) wherein $R^{7a}$ and $R^{8a}$ are benzyl groups and $R^9$ is a t-butoxycarbonyl group.

(34) A hydrazone derivative represented by the general formula [III-c]:

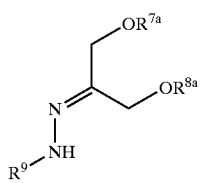

[III-c]

wherein $R^{7a}$ and $R^{8a}$ may be the same or different and each represent a protective group of a hydroxyl group, and $R^9$ represents a protective group of an amino group.

(35) The compound according to item (34) wherein $R^{7a}$ and $R^{8a}$ are benzyl groups and $R^9$ is a t-butoxycarbonyl group.

(36) The process according to item (21) wherein the hydrazinediol derivative represented by the general formula [III-b] is obtained by reacting a propanediol derivative represented by the general formula [III-g]:

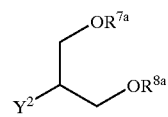

[III-g]

wherein $R^{7a}$ and $R^{8a}$ may be the same or different and each represent a protective group of a hydroxyl group, and $Y^2$ represents an eliminable group,
with a hydrazine derivative represented by the general formula [III-d]:

[III-d]

wherein $R^9$ represents a protective group of an amino group, in an inert solvent.

BEST MODE FOR CARRYING OUT THE INVENTION

This invention is specifically and detailedly described below.

Description is made below on terminology used in the specification.

The "alkyl group having 1 to 4 carbon atoms" means a straight-chain or branched alkyl group such as, for example, a methyl group, an ethyl group, a propyl group, an isopropyl group, a butyl group, an isobutyl group or a t-butyl group, and among them preferred is a methyl group, an ethyl group, a propyl group, an isopropyl group, a butyl group or the like, and further preferred is a methyl group, an ethyl group, a propyl group, an isopropyl group or a butyl group.

The "aralkyl group" means an aralkyl group having 7 to 12 carbon atoms such as, for example, a benzyl group, a 1-naphthylmethyl group or a 2-naphthylmethyl group, and preferred is a benzyl group.

The "acid molecule" means a protonic acid such as, for example, hydrochloric acid, sulfuric acid, nitric acid, acetic acid, methylsulfonic acid, p-toluenesulfonic acid, oxalic acid or propionic acid, and preferred is oxalic acid.

The "a protective group of a hydroxyl group" includes a protective group of a hydroxyl group such as, for example, a benzyl group, a p-nitrobenzyl group, a p-methoxybenzyl group or a benzyloxymethyl group, and preferred is a benzyl group.

The "a protective group of an amino group" includes a protective group of a hydroxyl group such as, for example, a methoxycarbonyl group, an ethoxycarbonyl group, a t-butoxycarbonyl group or a benzyloxycarbonyl group, and preferred is a t-butoxycarbonyl group.

The first step of the preparation process of the invention, namely, the step comprising treating a compound represented by the general formula [V]:

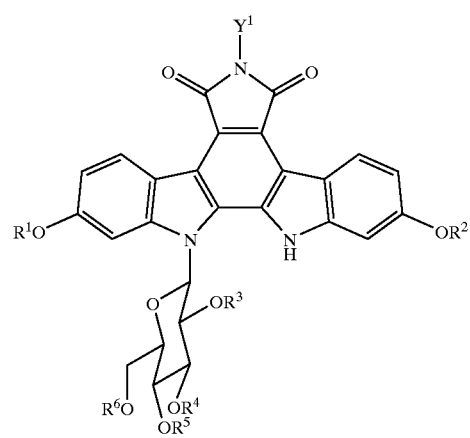

[V]

wherein $Y^1$ represents a hydrogen atom, an alkyl group having 1 to 4 carbon atoms, a phenyl group, a benzyloxymethyl group or an aralkyl group, and $R^1$, $R^2$, $R^3$, $R^4$, $R^5$ and $R^6$ may be the same or different and each represent a protective group of a hydroxyl group, and $R^7$ and $R^8$ may be the same or different and each represent a hydrogen atom or a protective group of a hydroxyl group, with a base in an inert solvent to prepare a compound represented by the general formula [IV]:

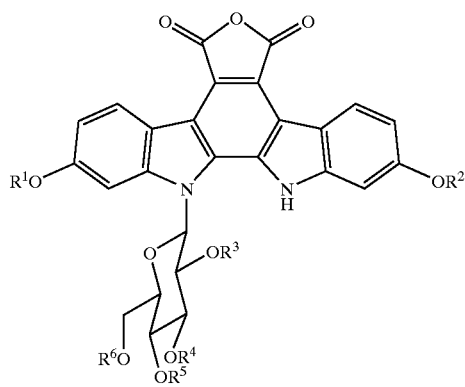

[IV]

wherein $R^1$, $R^2$, $R^3$, $R^4$, $R^5$ and $R^6$ are as defined above, is usually carried out in an inert solvent having no bad influence on the reaction, using 50 to 100 moles, preferably 50 to 70 moles of a base per 1 mole of the compound represented by the general formula [V].

As the inert solvent, there can, for example, be mentioned an alcohol such as methanol, ethanol, isopropanol or t-butanol; dimethylsulfoxide; or a mixed solvent thereof, etc., and particularly preferred is methanol, ethanol, isopropanol or the like.

As the base, there can be mentioned a base such as, for example, sodium hydroxide, potassium hydroxide, potassium methoxide, sodium methoxide, sodium t-butoxide or potassium t-butoxide, etc., and particularly preferred is sodium hydroxide, potassium hydroxide, sodium methoxide or the like.

The reaction temperature is, usually, room temperature to about 60° C., preferably 30° C. to 50° C., and the reaction time is, usually, 1 hour to 1 day, preferably, 3 hours to 10 hours.

The compound represented by the general formula [V] as the raw material used in the above step can be prepared or obtained, for example, by the process described in WO95/30682 or the like.

The step comprising reacting the compound [IV] obtained by the above step with a hydrazinediol derivative acid addition salt represented by the general formula [III]:

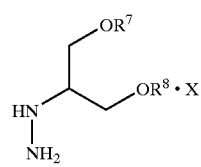

[III]

wherein X represents an acid molecule, and $R^7$ and $R^8$ may be the same or different and each represent a hydrogen atom or a protective group of a hydroxyl group, in the presence of an acid-capturing agent to prepare a compound represented by the general formula [II]:

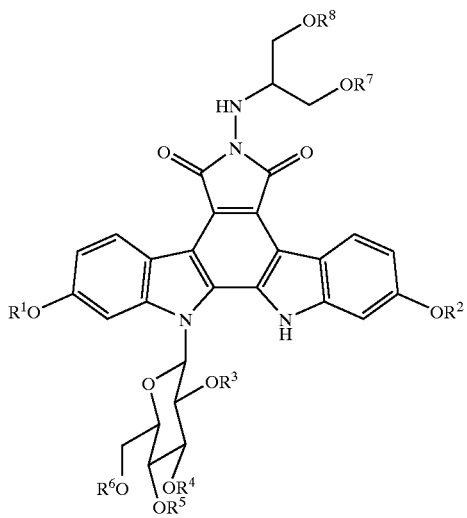

[II]

wherein $R^1$, $R^2$, $R^3$, $R^4$, $R^5$, $R^6$, $R^7$ and $R^8$ are as defined above, is usually carried out in an inert solvent having no bad influence on the reaction in the presence of an acid-capturing agent, using equimolar to 1.5 moles, preferably 1.2 to 1.3 moles of the compound of the general formula [III] per 1 mole of the compound of the general formula [IV].

As the inert solvent, there can, for example, be mentioned N,N-dimethylformamide, N,N-dimethylactamide, tetrahydrofuran, dimethylsulfoxide, N-methylpyrrolidone or a mixed solvent thereof, etc., and particularly preferred is N,N-dimethylformamide, N,N-dimethylactamide, N-methylpyrrolidone or the like.

The reaction temperature is, usually, room temperature to about 60° C., preferably about 30° C. to 50° C., and the reaction time is, usually, 1 hour to 1 day, preferably, 1 hour to 3 hours.

As the acid-capturing agent, there can, for example, be mentioned triethylamine or 4-dimethylaminopyridine, and preferred is triethylamine.

As to the step comprising removing the protective groups of the compound [II] obtained in the above step to prepare an indolopyrrolocarbazole derivative represented by the formula [I]:

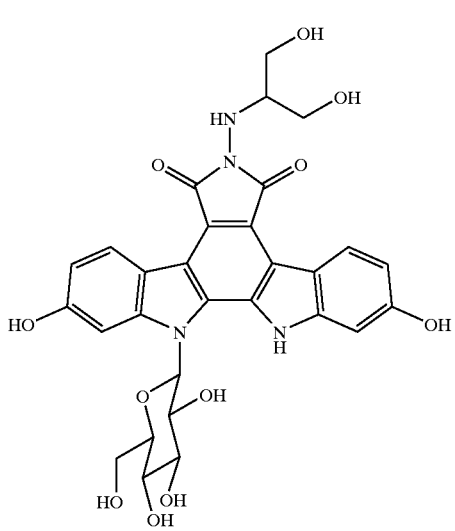

[I]

, when this reaction is carried out by catalytic reduction, the catalyst includes, for example, palladium-carbon catalyst, Raney nickel catalyst or the like.

The hydrogen pressure in the catalytic reduction is, usually, preferably normal pressure to 2 atoms, and the use amount of the catalyst is usually 1/100 to 1 times, preferably 1/100 to 1/10 times the weight 1 of the compound represented by the general formula [II] as the raw material.

As the reaction solvent, there can, for example, be mentioned a mixed solvent of an alcoholic solvent such as methanol, ethanol or butanol with tetrahydrofuran, and preferred is a mixed solvent of methanol/tetrahydrofuran (50/50).

The reaction temperature is, usually, about −30° C. to 60° C., preferably about 0° C. to 50° C., and the reaction time is, usually, instantaneous to 7 days, preferably instantaneous to 24 hours.

Each of compounds obtained in the above preparation steps can be purified or isolated by using methods known per se, namely commonly used separation or purification methods such as, for example, column chromatography, liquid chromatography or thin layer chromatography each using silica gel or an adsorption resin, solvent extraction and recrystallization or reprecipitation, according to necessity solely or in an appropriate combination of two or more.

Description is made below on respective steps for preparation of a hydrazinediol derivative acid addition salt represented by the general formula [III]:

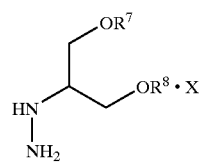

[III]

wherein X represents an acid molecule, and $R^7$ and $R^8$ may be the same or different and each represent a hydrogen atom or a protective group of a hydroxyl group, which is one of the raw material compounds in the preparation process of the invention.

The step of preparing a dihydroxyacetone derivative represented by the general formula [III-e]:

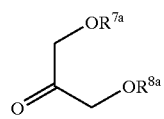

[III-e]

wherein $R^{7a}$ and $R^{8a}$ may be the same or different and each represent a protective group of a hydroxyl group, by reacting a propanetriol derivative represented by the general formula [III-f]:

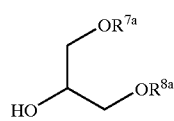

[III-f]

Wherein $R^{7a}$ and $R^{8a}$ are as defined above, with a hypochlorite in an inert solvent in the presence of a buffer can be carried out by adding the catalyst and the buffer to the inert solvent, adding the hypochlorite at −30° C. to 50° C., preferably −10° C. to 10° C. over a period of 1 hour to 3 hours, preferably 1.5 hours to 2 hours, and making reaction at the same temperature for 1 hour to 3 hours, preferably 1.5 hours to 2 hours.

It is possible to use, per 1 mole of the propanetriol derivative represented by the general formula [III-f], 0.005 mole to 1.0 mole, preferably 0.05 mole to 0.15 mole of the catalyst, 0.5 mole to 2.0 moles, preferably 1.0 mole to 1.5 moles of the buffer and 0.5 mole to 2.0 moles, preferably 1.0 mole to 1.5 moles of the hypochlorite.

As the inert solvent used in the step, there can, for example, be mentioned dimethylsulfoxide, dimethylformamide, dimethyl-acetamide, acetonitrile, propionitrile, toluene, xylene or benzene, etc., and preferred is acetonitrile or propionitrile.

As the catalyst used in the step, there can be mentioned

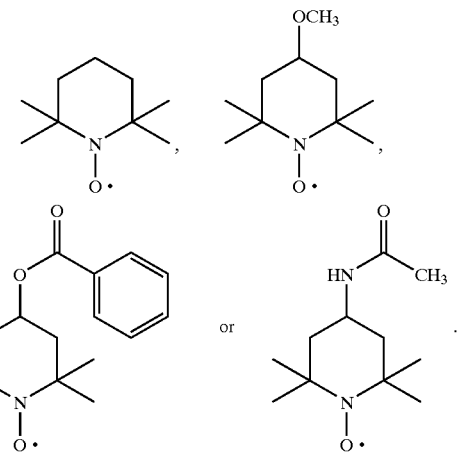

The catalysts are on the market or known compounds described in literatures, and are available.

As the buffer used in the step, any buffer can be used as long as change of the pH of the reaction mixture by addition of the hypochlorite can be inhibited, but there can be mentioned a 0.5% to saturated aqueous sodium bicarbonate solution, a phosphate buffer solution or the like.

As the hypochlorite used in the step, there can, for example, be used sodium hypochlorite, potassium hypochlorite, calcium hypochlorite or the like.

The raw material used in the step (the compound represented by the general formula [III-f]) can be prepared according to a known process (Canadian Journal of Chemistry, vol. 62, page 241 (1984)) or a commercial product can also be utilized.

As to this step, in the case of a known process (Tetrahedron, vol. 55, page 739 (1999)), it is carried out to adjust a sodium hypochlorite solution, prepared separately from the reaction solution, with sodium bicarbonate to pH 9.5 and, immediately thereafter, add the mixture to the reaction solution. In this case, there were a drawback that since chlorine gas is formed at the pH adjustment, the process is not proper as an industrial preparation process and a drawback that since it is difficult to add the hypochlorite with accuracy, impurities are formed by excessive oxidation. In this invention, by previously adding the buffer to the reaction solution and gradually adding the hypochlorite, the drawbacks of the known process can be obviated and the yield of the step can be increased.

The step of preparing a hydrazone derivative represented by the general formula [III-c]:

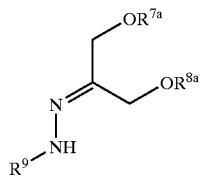

[III-c]

wherein $R^{7a}$ and $R^{8a}$ are as defined above, and $R^9$ represents a protective group of an amino group, by reacting the thus obtained dihydroxyacetone derivative represented by the general formula [III-e] with a hydrazine derivative represented by the general formula [III-d]:

[III-d]

wherein $R^9$ is as defined above, in a mixed solvent can be carried out by making reaction in the mixed solvent at 70° C. to 80° C., preferably 70° C. to 75° C. for 1 hour to 3 hours, preferably 1 hour to 1.5 hours.

The hydrazine derivative represented by the general formula [III-d] can be used in a ratio of 1.0 mole to 8.0 moles, preferably 1.1 moles to 1.5 moles per 1 mole of the dihydroxyacetone derivative represented by the general formula [III-e].

The mixed solvent used in the step is a mixed solvent obtained by mixing benzene, toluene, ethanol, isopropanol, acetonitrile or the like with an aliphatic hydrocarbon such as hexane or heptane in a ratio of 50:1 to 10:1 (volume ratio), preferably 30:1 to 20:1 (volume ratio).

In a known process (Journal of Organic Chemistry, vol.46, page 5413 (1981)), this step is carried out under a reaction condition such as reflux for 20 minutes in a single solvent (hexane). But, when the step is carried out under such a condition, there arise such problems that the purity of the hydrazone derivative prepared is low, and that the by-products formed remain in the final product.

According to the present invention, the problems of the known process can be obviated by, after the reaction at 70° C. to 80° C. for 1 hour to 3 hours in the mixed solvent, crystallizing the hydrazone derivative represented by the general formula [III-c] at 60° C. and gradually lowering the temperature of the reaction mixture to room temperature.

The step of preparing a hydrazinediol derivative represented by the general formula [III-b]:

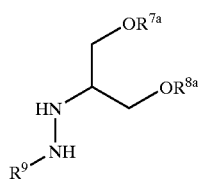

[III-b]

wherein $R^{7a}$ and $R^{8a}$ may be the same or different and each represent a protective group of a hydroxyl group, and $R^9$ represents a protective group of an amino group, by reducing a hydrazone derivative represented by the general formula [III-c]:

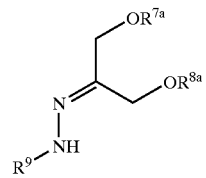

[III-c]

wherein $R^{7a}$, $R^{8a}$ and $R^9$ are as defined above, can be carried out by reacting 2- to 5-fold moles of a reducing agent at 0° C. to 80° C., preferably 0° C. to 70° C. for 30 minutes to 48 hours, preferably 1 hour to 41 hours in the presence or absence of an inert solvent.

As the inert solvent used in the step, there can be mentioned an organic solvent such as, for example, heptane, hexane, methanol, ethanol or tetrahydrofuran, and preferred is tetrahydrofuran, ethanol or in the absence thereof.

As the reducing agent used in the step, there can be mentioned a reducing agent such as, for example, $BH_3$-tetrahydrofuran complex, $NaBH_4$, $NaHB(OAc)_3$, $NaH_3BCN$, diborane, $BH_3$-dimethylsulfide, Raney nickel, diisobutylaluminum hydride (DIBAL), $Zn(BH_4)_2$, $LiBH_4$, Pt—S/C or $LiAlH_4$, and preferred is $BH_3$-tetrahydrofuran complex or $NaBH_4$.

When the reducing agent is a boron compound, for accelerating the generation of $BH_3$ in the reaction system, it is possible to add 0.5 to 1.0 mole of, for example, $BF_3$, $BCl_3$, sulfuric acid, methanesulfonic acid, p-toluenesulfonic acid, hydrochloric acid, aluminum chloride, zinc chloride, dimethyl sulfate, diethyl sulfate, methyl iodide or the like per 1.0 mole of the reducing agent.

The step of eliminating the protective group of the amino group ($R^9$) of the hydrazinediol derivative represented by the general formula [III-b]:

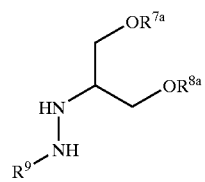

[III-b]

wherein $R^{7a}$, $R^{8a}$ and $R^9$ are as defined above, can be carried out by making 2 to 20 equivalents of an inorganic acid act in a solvent such as, for example, tetrahydrofuran at 50° C. to 100° C. for 3 hours to 24 hours.

As the inorganic acid, there can, for example, be mentioned hydrochloric acid, sulfuric acid or nitric acid, and preferred is 6-normal hydrochloric acid.

The step of preparing a hydrazinediol derivative acid addition salt represented by the general formula [III']:

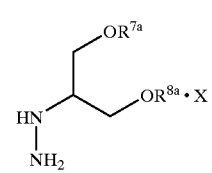

[III']

wherein $R^{7a}$ and $R^{8a}$ may be the same or different and each represent a protective group of a hydroxyl group, and X represents an acid molecule, by reacting the thus obtained hydrazinediol derivative represented by the general formula [III-a]:

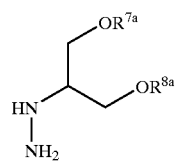
[III-a]

wherein $R^{7a}$ and $R^{8a}$ are as defined above, with an acid can be carried out by reacting 0.5 equivalent to 2 equivalents of an acid in an inert solvent such as, for example, methyl t-butyl ether or a mixed solvent of methyl t-butyl ether with methanol at room temperature to 40° C. for 30 minutes to 2 hours.

As the acid used in the step, there can, for example, be mentioned a protonic acid such as hydrochloric acid, sulfuric acid, nitric acid, acetic acid, methylsulfonic acid, p-toluenesulfonic acid, oxalic acid or propionic acid, and preferred is oxalic acid.

The step of preparing a hydrazinediol derivative represented by the general formula [III-b]:

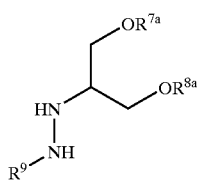
[III-b]

wherein $R^{7a}$ and $R^{8a}$ may be the same or different and each represent a protective group of a hydroxyl group, and $R^9$ represents a protective group of an amino acid, by reacting a propanediol derivative represented by the general formula [III-g]:

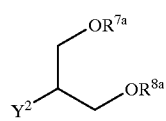
[III-g]

wherein $R^{7a}$ and $R^{8a}$ are as defined above, and $Y^2$ represents an eliminable group,
with a hydrazine derivative represented by the general formula [III-d]:

[III-d]

wherein $R^9$ is as defined above, in an inert solvent can be carried out by carrying out the reaction in an inert solvent such as, for example, N,N-dimethylformamide, tetrahydrofuran, N-methylpyrrolidone or dimethylsulfoxide at 80° C. to 150° C., preferably 100° C. to 120° C. for 50 hours to 100 hours, preferably 70 hours to 80 hours.

The use amount of the hydrazine derivative represented by the general formula [III-d] is 1 equivalent to 20 equivalents, preferably 1.5 equivalents to 3 equivalents based on the propanetriol derivative represented by the general formula [III-g]

The eliminable group represented by $Y^2$ means an eliminable group such as, for example, a methylsulfonyloxy group, a chloromethylsulfonyloxy group, a p-toluenesulfonyloxy group, a trifluoromethylsulfonyloxy group or a p-nitrobenzene-sulfonyloxy group.

The propanetriol derivative represented by the general formula [III-g] can be obtained by a process described in a literature such as, for example, Journal of the Chemical Society Perkin Transaction-I, page 2757 (1988) or a process applying the former process similarly.

In the hydrazine derivative acid addition salt represented by the general formula [III]:

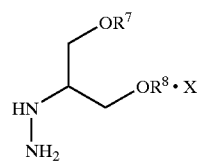
[III]

wherein X represents an acid molecule, and $R^7$ and $R^8$ each represent a hydrogen atom or a protective group of a hydroxyl group,
as one of the raw material compounds in the preparation process of the invention, the compound wherein $R^7$ and $R^8$ are hydrogen atoms can be prepared by preparing a compound represented by the formula [VIII]:

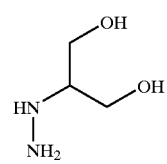
[VIII]

according to the preparation process disclosed in WO95/30682 and carrying out the same treatment as in the aforementioned step where a hydrazinediol derivative represented by the general formula [III-a] is converted to its acid addition salt.

Compounds obtained in the above respective preparation steps can be purified or isolated by methods known per se, namely by using commonly used separation or purification methods such as, for example, column chromatography, liquid chromatography or thin layer chromatography using silica gel, an adsorption resin or the like, solvent extraction, and recrystallization or reprecipitation, alone or in an appropriate combination thereof according to necessity.

Description is made below on usefulness of the preparation process of the invention as an industrial preparation process.

The compound represented by the formula [VIII]:

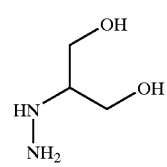
[VIII]

, which is a known compound (disclosed in WO95/30682), is an oily substance and low in stability, and from reasons as above, must be stored in an solvent at low temperatures, whereas the hydrazinediol derivative acid addition salt represented by the general formula [III]:

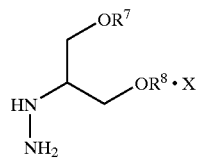

[III]

wherein X represents an acid molecule, and $R^7$ and $R^8$ each represent a hydrogen atom or a protective group of a hydroxyl group, which is one of the preparation raw materials of the invention, is in the form of crystals, and thus is easy to isolate and has high stability, and therefore, possesses more suitable properties and state than the known substance for industrial preparation.

And as apparent from the experimental results of Table 1, the preparation intermediates according to the preparation process of the invention are far lower in inhibitory activity on topoisomerase I than the intermediates in the known process (the preparation process disclosed in WO95/30682), and therefore can be prepared using usual facilities and it is possible to reduce a danger that workers relating to the preparation steps are exposed to highly active compounds. Therefore, the preparation process of the invention can be said to be an industrial preparation process excellent in the aspect of the preparation facilities and the aspect of safety of the workers, compared with the known process.

TABLE 1

Topoisomerase I-inhibiting activity

| Test compound | $EC_{50}$ (µM) |
| --- | --- |
| Desired compound of Example 1 | >1,000 |
| Desired compound of Example 2 | >1,000 |
| Comparative example (Compound [b]) ($R^a$ = methyl group) | 0.68 |
| Comparative example (Compound [c]) | 0.18 |

Topoisomerase I-inhibiting activity was assayed by the method described in Yoshinari, T et al., Cancer Research, vol. 55, page 1310 (1995).

In the table, $EC_{50}$ means the concentration of a compound needed to inhibit topoisomerase I activity by 50%.

EXAMPLES

The invention is further specifically described below according to examples and reference examples, but the invention is not limited thereby at all. Bn and Boc mean a benzyl group and a t-butoxycarbonyl group, respectively.

Example 1

Preparation of 12,13-dihydro-2,10-dibenzyloxy-13-(β-D-2, 3,4,6-tetra-O-benzylglucopyranosyl)-5H-indolo[2,3-a] carbazole-5,6-dicarboxylic anhydride

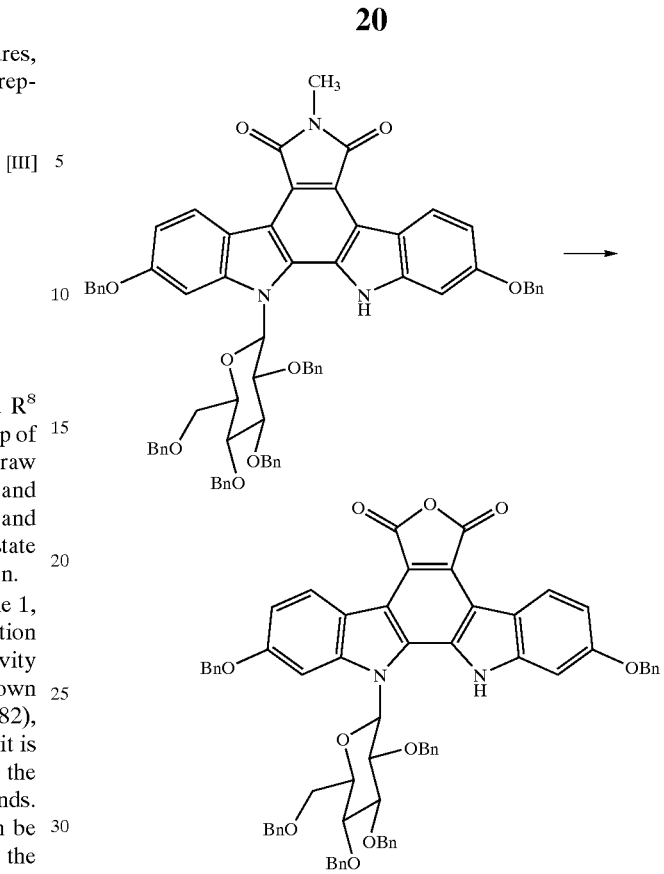

A stirrer and a thermometer were set in a 300-mL four-necked flask, and 36 mL (milliliter) of ethanol was put in. While stirring the ethanol, 12,13-dihydro-2,10-dibenzyloxy-13-(β-D-2,3,4,6-tetra-O-benzylglucopyranosyl)-5H-indolo[2,3-a]-pyrrolo [3,4-c]carbazole-6-methyl-5,7(6H)-dione (670 mg, 0.62 mmol) was put in and the mixture was stirred at room temperature for 1 hour. 5N-aqueous potassium hydroxide solution (8 mL) was added dropwise at that temperature over a period of 20 minutes. The inside temperature was made to be 60° C. and the mixture was stirred for 4 hours and then stirred at room temperature overnight. Toluene (20 mL) was added to the brown solution obtained, and at that temperature 1.0 N-hydrochloric acid (62 mL) was added dropwise over a period of 30 minutes, and the mixture was made to be pH 2.6. Tetrahydrofuran (10 mL) was added to this yellow solution and the mixture was stirred for 6 hours. The water layer (the lower layer) was separated, and the organic layer was washed with purified water (10 mL×2 times) and saturated saline (saline is aqueous sodium chloride solution) (10 mL) in this order, dried over anhydrous sodium sulfate (5 g) and filtered. The solvent was distilled off under reduced pressure to obtain the desired compound 12,13-dihydro-2,10-dibenzyloxy-13-(β-D-2,3,4, 6-tetra-O-benzylglucopyranosyl)-5H-indolo[2,3-a]-carbazole-5,6-dicarboxylic anhydride (0.63 g; yield 85%) as a yellow oily residue.

$^1$H-NMR(270 MHz, CDCl$_3$, δ ppm):10.79(1H, br.s,),9.04 (1H,d, J=9.2 Hz),8.95(1H,d,J=9.6 Hz),7.26(32H,m),6.17 (2H,d, J=7.3 Hz),5.85(1H,d,J=8.2 Hz),4.89(10H,m),4.32 (1H,t, J=8.9 Hz),3.96(6H,m),3.13(1H,d,J=10.2 Hz)

Example 2

Preparation of 12,13-dihydro-2,10-dibenzyloxy-6-N-(1-hydroxymethyl-2-hydroxyethylamino)-13-(β-D-2, 3,4, 6-tetra-O-benzylglucopyranosyl)-5H-indolo[2.3-a]pyrrolo[3,4-c]-carbazole-5,7(6H)-dione

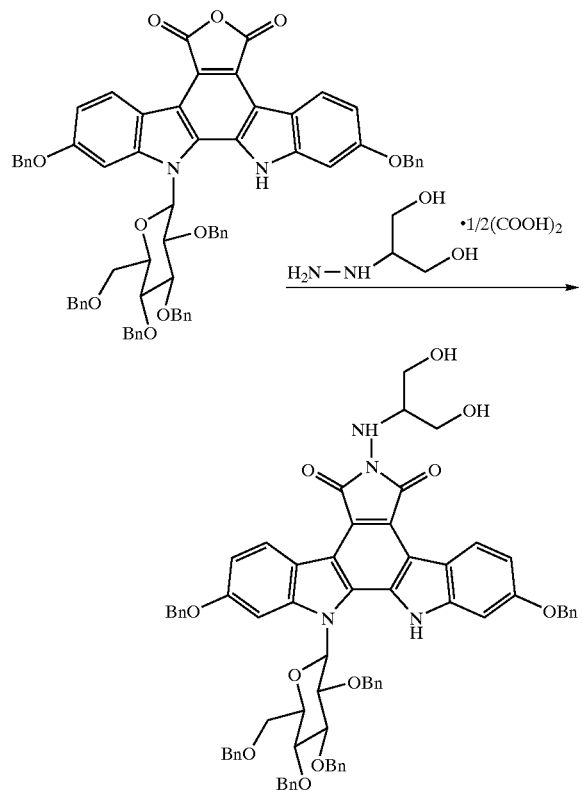

12, 13-dihydro-2,10-dibenzyloxy-13-(β-D-2,3,4,6-tetra-O-benzylglucopyranosyl)-5H-indolo[2,3-a]carbazole-5,6-dicarboxylic anhydride (1.46 g) obtained in Example 1 and N,N-dimethylacetamide (15 mL) were placed in a 50-mL three-necked flask. While stirring the mixture, N-(1-hydroxy-methyl-2-hydroxyethyl)hydrazine oxalate (0.23 g) and triethylamine were added. The inside temperature was made to be 60° C., the mixture was stirred for 1.5 hours and cooled to room temperature. Methyl t-butyl ether (10 mL) and purified water (5 mL) were added to the obtained orange solution, and the mixture was stirred for 30 minutes. The water layer (lower layer) was separated, and the organic layer was washed with water (5 mL ×2 times) and saturated saline (10 mL) in this order, dried over anhydrous sodium sulfate (5 g), and filtered. The solvent was distilled off under reduced pressure to obtain the desired compound 12,13-dihydro-2,10-dibenzyloxy-6-N-(1-hydroxy-methyl-2-hydroxyethylamino)-13-(β-D-2,3,4,6-tetra-O-benzyl-glucopyranosyl)-5H-indolo[2,3-a]pyrrolo[3,4-C]carbazole-5,7(6H)-dione (1.47 g; yield 92%) as an orange residue.

[1] H-NMR(270 MHz,CDCl$_3$), δ(ppm):10.68(1H, br.s,), 9.14(1H,d, J=9.2 Hz),9.05(1H,d,J=9.6 Hz),7.27(32H,M), 6.20(2H,d, J=6.9 Hz),5.83(1H,d,J=8.9 Hz),4.87(1H,m),4.32 (1H,t, J=9.4 Hz),3.77(13H,m),3.05(1H,d,J=9.9 Hz)

Example 3

Preparation of 12,13-dihydro-2,10-dihydroxy-6-N-(1-hydroxymethyl-2-hydroxyethylamino)-13-(β-D-glucopyranosyl)-5H-indolo[2,3-a]pyrrolo[3,4-c]carbazole-5,7(6H)-dione

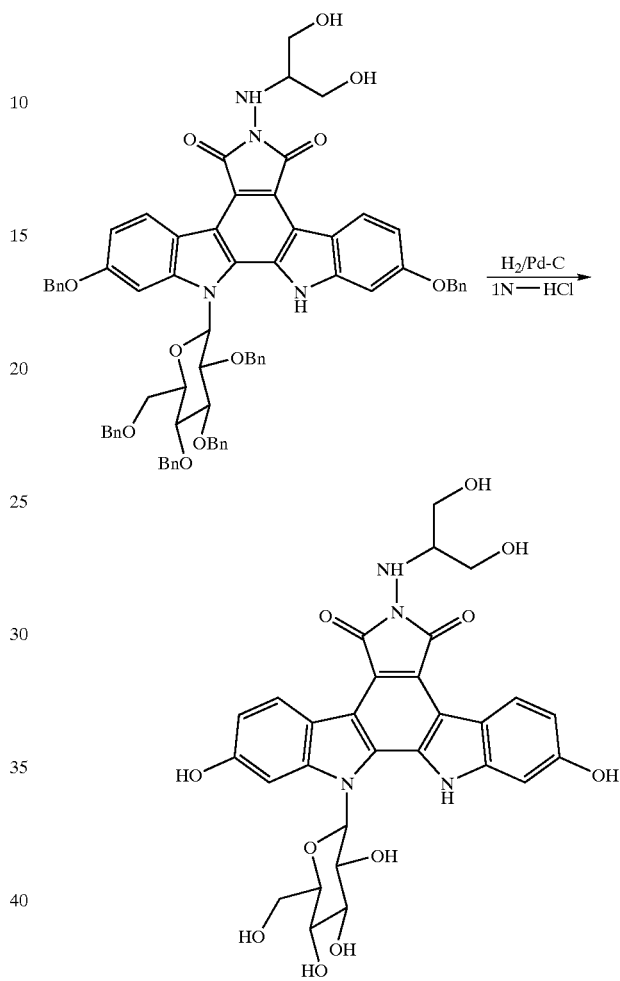

12,13-dihydro-2,10-dibenzyloxy-6-N-(1-hydroxymethyl-2-hydroxyethylamino)-13-(β-D-2,3,4, 6-tetra-O-benzyl-glucopyranosyl)-5H-indolo[2,3-a]pyrrolo[3,4-c]carbazole-5,7(6H)-dione (500 mg) obtained in Example 2 and methanol/tetrahydrofuran (50/50) (10 mL) were placed in a hydrogenating apparatus, and after confirmation of dissolution, 10% palladium-carbon (100 mg) and 1 N-hydrochloric acid (100 μL) (μL: microliter) were added. After three times replacement with hydrogen, the hydrogen pressure was fixed at 29.4 pascals, the inside temperature was made to be 40° C., and the mixture was stirred for 3 hours. The palladium-carbon was filtered, active carbon (50 mg) was added to the filtrate and the mixture was stirred for 1 hour. After filtration of the active carbon, purified water (1 mL) and heptane (40 mL) were added, and the resulting two layers were separated. The water layer was concentrated to 1 mL to distill off the solvent and under stirring of the concentrate, methanol (3 mL) was gradually added dropwise. The resulting suspension (amorphous deposition) was heated to 90° C., refluxed for 9 hours, cooled to room temperature, and stirred overnight. The suspension was filtered to obtain an amorphous substance (amorphous, orange, 170 mg; yield 64%). Methanol (3 mL) was added to the amorphous substance, and the mixture was refluxed for 9 hours, cooled to room temperature, and stirred overnight. The suspension was filtered to obtain a yellow crystalline substance (100 mg; yield 59%). By coincidence of the mass spectrum, infrared absorption spectrum and nuclear magnetic resonance spectrum of this yellow crystalline substance with those of the compound described in Example 1 of WO95/30682, the yellow crystalline substance was identified as 12,13-dihydro-2,10-dihydroxy-6-N-(1-hydroxymethyl-2-hydroxyethyl-amino)-13-(β-D-glucopyranosyl)-5H-indolo[2,3-a]pyrrolo[3,4-c]carbazole-5,7(6H)-dione.

Example 4

Preparation of 1,2-dihydroxyacetone t-butoxycarbonylhydrazone

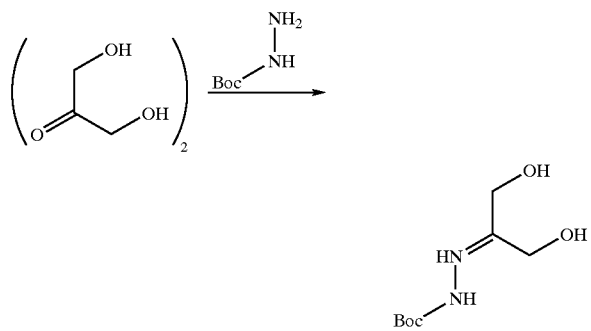

Ethanol (6 L) (L is liter), 1,3-dihydroxyacetone dimer (137.82 g, 0.765 mol) and t-butoxycarbonyl hydrazide (198.24 g, 1.5 mol) were placed in a 10-L four-necked flask equipped with a stirrer, a thermometer and a nitrogen gas-introducing tube at room temperature with stirring under a nitrogen gas stream. After the mixture was stirred at room temperature overnight, the reaction solution was concentrated at the outside temperature of 50° C. under reduced pressure to about 0.5 L. Ethyl acetate (2.5 L) was added to the concentrate and the mixture was concentrated to about 0.5 L under reduced pressure. Ethyl acetate (2.5 L) was further added and the mixture was concentrated to about 0.5 L under reduced pressure. Ethyl acetate (1.5 L) was added to the concentrate and the mixture was stirred at the outside temperature of 25° C. for 1 hour. The mixture was then cooled to 5° C. and stirred for 1 hour and 30 minutes, and the crystals deposited were obtained by filtration, washed with ethyl acetate (550 mL) and vacuum dried overnight at 40° C. to obtain 1,2-dihydroxyacetone t-butoxycarbonylhydrazone as colorless crystals (285.43 g; yield 93%).

$^1$H-NMR(270 MHz,DMSO-d6,),δ(ppm):9.97(1 H,br.s), 5.60(1H, br.s),4.87(1H,t,J=5.61 Hz),4.24(1H,br.s),3.93(2H, d, J=5.61 Hz),1.42(9H,s)

Example 5

Preparation of N-(1-hydroxymethyl-2-hydroxyethyl) hydrazine hemioxalate

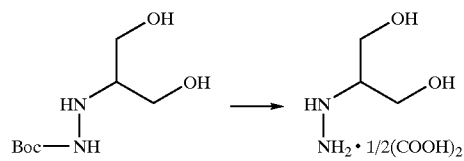

1,2-dihydroxyacetone t-butoxycarbonylhydrazone (102.11 g, 0.5 mol) and tetrahydrofuran (204 mL) were placed in a 3-L four-necked flask equipped with a stirrer, a Dimroth condenser, a dropping funnel, a thermometer and a nitrogen gas-introducing tube and set in an oil bath. 1 M borane-tetrahydrofuran complex solution (0.75 L, 0.75 mol) was added dropwise to this suspension at −4 to 3° C. over a period of 40 minutes. The reaction solution was stirred at −3 to 3° C. for 1 hour and 6-normal hydrochloric acid (208 mL) was added dropwise over a period of 15 minutes (the inside temperature rose by 11.2° C.). The reaction solution was boiled under reflux in the oil bath for 1 hour, cooled and stirred at 5° C. or less for 30 minutes. The reaction solution was concentrated to about 300 mL and the concentrate was left alone at 15° C. overnight. The deposited boric acid was filtered off and washed with purified water (100 mL×2). The filtrate and the washings were combined (about 500 mL) and subjected to Dowex 50 ×4 (about 1.5 L), the Dowex 50×4 was washed with water, and the desired product was eluted with 0.6 N ammonia water (6 L). The desired fractions (about 1.5 L) were collected and concentrated under reduced pressure until they got oily at the outside temperature of 45° C. Purified water (1.0 L) was added to the concentration residue obtained and the mixture was concentrated until it got oily at the outside temperature of 45° C. The concentrate was further concentrated at room temperature for 24 hours under reduced pressure to obtain N-(1-hydroxy-methyl-2-hydroxyethyl)hydrazine (49.6 g) as a colorless oily residue which solidified under cooling at −30° C.

The obtained solidified matter and methanol (250 mL) were placed in a 1-L four-necked flask under a nitrogen stream, and a solution obtained by dissolving oxalic acid (23.02 g, 0.28 mol) in methanol (250 mL) was added dropwise under stirring over a period of 22 minutes (the temperature rose from 17° C. to utmost 39.4° C.). The moment the dropwise addition was started, crystals deposited. After stirring at room temperature for 3 hours, the mixture was cooled to 5° C. and stirred for 1 hour. The crystals were taken by filtration, washed with methanol (250 mL) and dried at room temperature for 18 hours under reduced pressure to obtain the desired compound N-(1-hydroxymethyl-2-hydroxyethyl)-hydrazine hemioxalate (59.2 g; yield 78.3%) as colorless crystals.

$^1$H-NMR(270 MHz,D$_2$O), δ(ppm):3.69(2H,m),3.59(2H, m),3.20(1H,m)

Example 6

Preparation of N-(1-benzyloxymethyl-2-benzyloxyethyl)-hydrazine hemioxalate

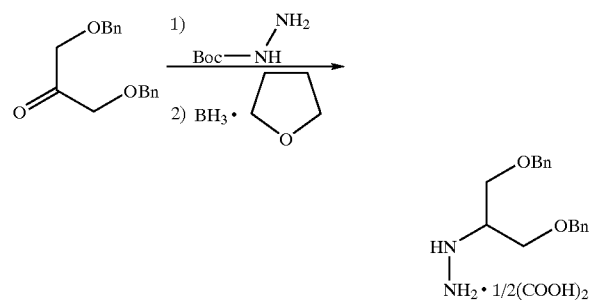

A mixed solution of 1,3-benzyloxy-2-propanone (113 g, 395 mmol) (see R. Csuk et al., Tetrahedron, vol. 55, pages 739–750 (1999)), t-butoxycarbonylhydrazine (57.4 g, 435 mmol) and heptane (1.57 L) was stirred under reflux for 1 hour and cooled to room temperature, and the product deposited was taken by filtration and dried under reduced pressure to obtain a hydrazone derivative (120 g; yield 78%).

$^1$H-NMR(270 MHz,CDCl$_3$, δ ppm):9.69(1H,br.s), 7.40–7.25(10H,m), 4.51(2H,s),4.49(2H,s),4.35(2H,s),4.12 (2H,s)

10.0 g (26.0 mmol) of the obtained hydrazone derivative was taken, borane-tetrahydrofuran (1 M solution in tetrahydrofuran, 78 mL, 78 mmol) was added dropwise, the mixture was stirred at room temperature for 1 hour and cooled to 8° C., and 6-normal hydrochloric acid (42 mL) was added dropwise. The mixture was stirred at the inside temperature of 65° C. for 10 minutes and cooled to 0° C., 10% sodium carbonate solution (280 mL) was added, and the mixture was extracted with methyl t-butyl ether (100 mL). The organic layer was washed with water, dried over sodium sulfate and filtered. Methyl t-butyl ether (90 mL) was added to the solution and a solution of oxalic acid (1.20 g, 13.3 mmol) in methanol (13 mL) was added dropwise over a period of 20 minutes. The mixture was stirred for 20 minutes, and the product deposited was taken by filtration and dried under reduced pressure to obtain the desired captioned compound (5.71 g; yield 66%).

$^1$H-NMR(270 MHz,CDCl$_3$,δ ppm):7.41–7.26(10H,m), 5.91–5.62(4H, br.m,moved by heavy water addition),4.50 (4H,s),3.56(4H,br.d, J=4.9 Hz),3.34(1H,m)
$^{13}$C-NMR(68 MHz,CDCl$_3$, δ ppm):164.7, 138.2, 128.2, 127.5, 127.4, 72.3, 68.3, 59.8

Example 7

Preparation of 12,13-dihydro-2,10-dibenzyloxy-6-N-(1-benzyloxymethyl-2-benzyloxyethylamino)-13-(β-D-2, 3,4,6-tetra-O-benzylglucopyranosyl)-5H-indolo [2,3-a]pyrrolo-[3,4-c]carbazole-5,7(6H)-dione

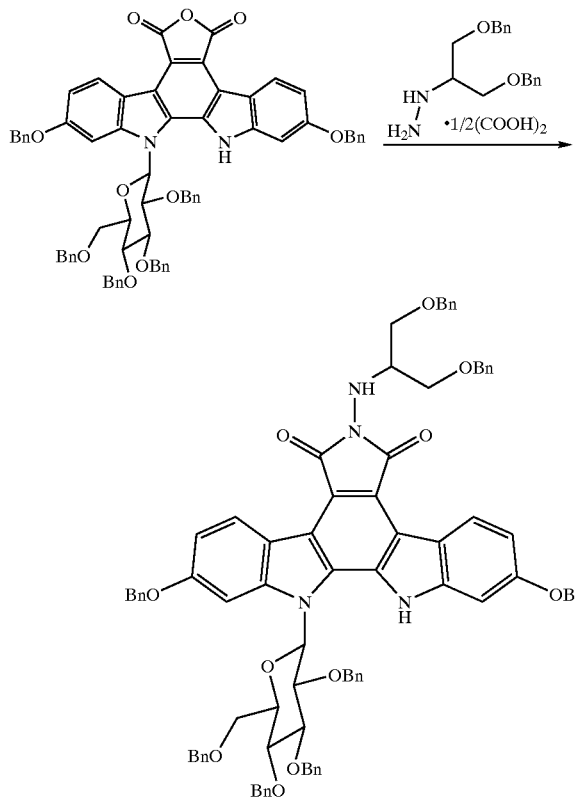

A mixture of 12,13-dihydro-2,10-dibenzyloxy-13-(β-D-2,3,4,6-tetra-O-benzylglucopyranosyl)-5H-indolo[2,3-a]-carbazole -5,6-dicarboxylic anhydride (1.00 g, 0.94 mmol) obtained in Example 1, N-(1-benzyloxymethyl-2-benzyloxyethyl)hydrazine hemioxalate (398 mg, 1.20 mmol) and N,N-dimethylacetamide (9.2 mL) was deaerated and after replacement with nitrogen heated to 62° C. Triethylamine (0.17 mL, 1.20 mmol) was added dropwise to this solution, the mixture was stirred at that temperature for 3 hours and cooled to room temperature, and methyl t-butyl ether (20 mL) and water (4.7 mL) were added. The water layer was made to pH 4 with 1 N-aqueous hydrochloric acid solution and stirred for 20 minutes. The organic layer was separated, washed five times with water (6 mL), dried over sodium sulfate and filtered. Finally, the filtrate was concentrated under reduced pressure to obtain the desired compound (1.29 g) in a crude state.

$^1$H-NMR(270 MHz,CDCl$_3$,δ ppm):10.63(1 H,br.s),9.24(1 H,br.d, J=9.6 Hz),9.16(1H,br.d,J=9.6 Hz),7.50–6.84(42H, m),6.20(2H, br.d,J=7.6 Hz),5.84(1H,d,J=8.6 Hz),5.33(1H, br.d,J=3.0 Hz), 5.21(1H,d,J=12.2 Hz),5.19(1H,d,J=11.9 Hz), 5.16(1H,d, J=12.2 Hz),5.08(1H,d,J=11.9 Hz),5.08(1H,d,J= 10.9 Hz),4.96(1H, d,J=10.9 Hz),4.89(1H,d,J=10.9 Hz),4.85 (1H,d,J=10.9 Hz), 4.72(1H,d,J=12.9 Hz),4.68(1H,d,J=12.9 Hz),4.62–4.48(4H,m), 4.33(1H,dd,J=9.6, 9.6 Hz),4.06–3.77 (7H,m),3.72(4H,d, J=5.6 Hz),3.04(1H,d,J=9.9 Hz)

$^{13}$C-NMR(68 MHz,CDCl$_3$, δ ppm):168.8, 168.7, 159.4, 159.3, 143.2, 142.9, 138.0, 137.9, 137.6, 136.9, 136.8, 136.6, 136.0, 130.2, 128.7, 128.6, 128.5, 128.4, 128.3, 128.2, 128.2, 128.1, 128.0, 127.9, 127.8, 127.7, 127.6, 127.5, 127.4, 127.3, 126.9, 126.6, 119.4, 119.1, 118.0, 116.9, 116.7, 116.1, 110.4, 96.7, 96.3, 85.8, 84.7, 80.9, 77.4, 77.2, 76.0, 75.9, 75.4, 74.9, 73.9, 73.3, 73.2, 70.7, 70.4, 69.9, 69.8, 66.7, 58.7, 49, 4, 30.9, 27.0

Example 8

Preparation of 12,13-dihydro-2.10-dihydroxy-6-N-(1-hydroxymethyl-2-hydroxyethylamino)-13-(β-D-glucopyranosyl)-5H-indolo[2,3-a]pyrrolo[3,4-c]carbazole-5,7(6H)-dione

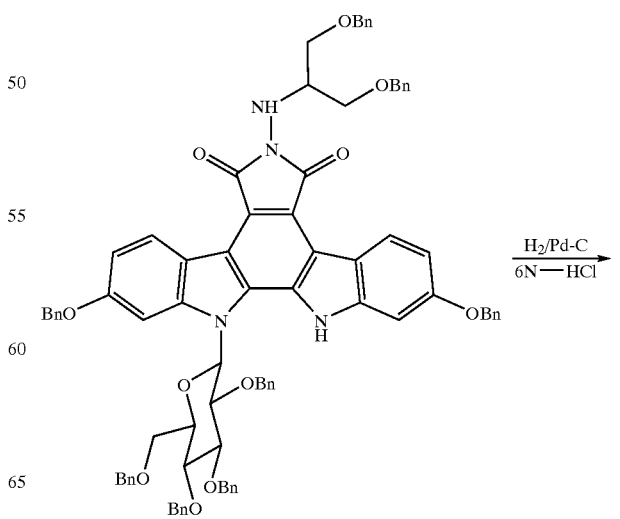

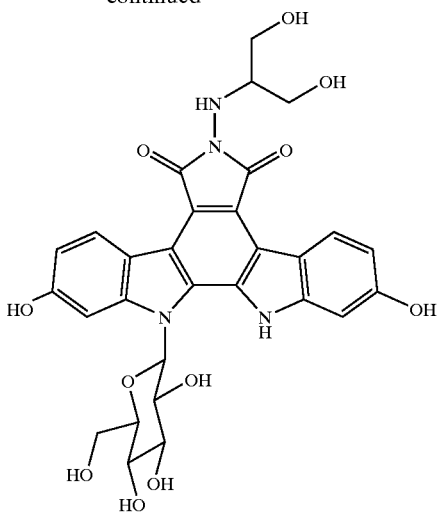

12,13-dihydro-2,10-dibenzyloxy-6-N-(1-benzyloxymethyl-2-benzyloxyethylamino)-13-(β-D-2, 3,4, 6-tetra-O-benzyl-glucopyranosyl)-5H-indolo[2,3-a]pyrrolo [3,4-c]carbazole-5,7 (6H)-dione (600 mg) obtained in Example 7 and ethanol/tetrahydrofuran (50/50) mixed solvent (12 mL) were placed in a hydrogenating apparatus, and after confirmation of dissolution, 10% palladium-carbon (120 mg) and 6 N-hydrochloric acid (120 μL) were added. After three times replacement with hydrogen, the hydrogen pressure was fixed to 29.4 pascals and the inside temperature was made to 40° C., and the mixture was stirred for 3 hours. After filtration of the palladium-carbon, tributylphosphine (360, μL) was added, the mixture was stirred for 5 minutes, purified water (824 μL) and heptane (40 mL) were added, and the resulting two layers were separated. The water layer was concentrated to 824 μL to distill off the solvent, and methanol (5.5 mL) was gradually added dropwise under further stirring. The resulting suspension (amorphous deposition) was heated to 90° C. and refluxed for 9 hours, cooled to room temperature and stirred overnight. The suspension was filtered to obtain yellow crystals (175 mg; yield 64%). By coincidence of the mass spectrum, infrared absorption spectrum and nuclear magnetic resonance spectrum of the yellow crystals with those of the desired compound of Example 3, the desired compound of the present Example was identified as 12,13-dihydro-2,10-dihydroxy-6-N-(1-hydroxymethyl-2-hydroxyethylamino)-13-(β-D-glucopyranosyl)-5H-indolo[2,3-a]pyrrolo[3,4-c]carbazole-5,7(6H)-dione.

Example 9

Preparation of 1,3-dibenzyloxyacetone

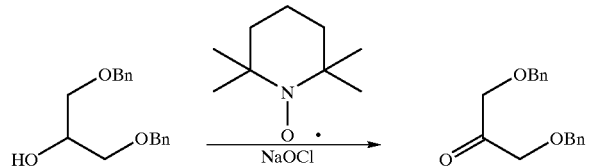

1,3-dibenzyloxy-2-propanol(100.0 g, 367 mmol), acetonitrile (1352 mL) and 2,2,6,6-tetramethyl-1-piperidinyloxy free radical (5.74 g, 36.7 mmol) were placed in a 5,000-mL four-necked flask equipped with a mechanical stirrer and a thermometer under a nitrogen stream, and the mixture was stirred for 5 minutes. Then, 3% aqueous sodium bicarbonate solution (1,028 g, 367 mmol) was added and the mixture was cooled to 1.1° C. using an ice bath. 11.9% aqueous sodium hypochlorite solution (when 10% aqueous sodium hypochlorite solution on the market was titrated, the accurate concentration was 11.9%) (276 g, 441 mmol) was added to the mixture over a period of more than 2 hours while keeping the temperature of the mixture at 5° C. or less (the reaction was a little exothermic), and the mixture was stirred at from 0.5° C. to 2.0° C. for 1 hour. Methyl t-butyl ether (2,700 mL) was added to the reaction mixture, the mixture was stirred for 20 minutes while keeping the temperature at 10° C. or less and allowed to stand for 10 minutes, and the resulting two layers were separated (the water layer weighed 1, 289 g and its pH was 8). The obtained organic layer was washed with 10% aqueous sodium sulfite solution (330 g), 5% saline (200 g) and 20% saline (200 g) in this order. The resulting solution (3,130 g) was analyzed by high performance liquid chromatography and as a result 91.8 g (yield 93%) of the captioned 1,3-dibenzyloxypropanone was obtained.

$^1$H-NMR(270 MHz, CDCl$_3$,δ ppm):7.35–7.26(m,10H), 4.57(s,4H), 4.24(s,4H)

The solution was stored overnight at 5° C. The solution was concentrated to 500 mL under reduced pressure using a water bath of 40° C., heptane (500 mL) was added, and the mixture was concentrated to 500 mL under reduced pressure at 40° C., and the above step was repeated twice, heptane was added to adjust the liquid amount of the concentrate to 500 mL, and the mixture was used in the next step without purification.

Measurement condition of high performance liquid chromatography:

Column: Zorbax SB-CN

Measurement temperature: 25° C.

Mobile phase: 0.1% pH 7 phosphate buffer solution-acetonitrile (T=0 minute, 50:50 (T=15 minutes, composition of mobile phase: 50:50 (T=25 minutes, composition of mobile phase: 5:95)

Flow rate: 1.0 mL/min

Detection wavelength: 220 nm

Example 10

Preparation of 1,3-dibenzyloxyacetone t-butyloxycarbonyl-hydrazone

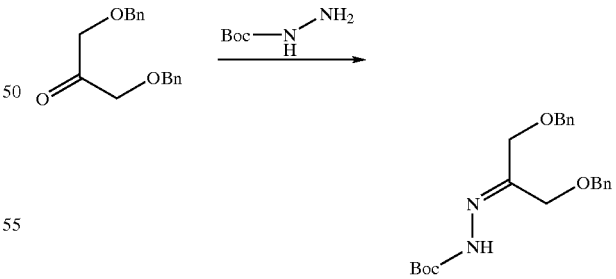

The mixture (91.8 g, 335 mmol) obtained in Example 9 was placed in a 5,000-mL four-necked flask equipped with a Dimroth condenser, a mechanical stirrer and a thermometer, heptane (2,100 mL) was added and the mixture was stirred. The mixture was heated at 55° C. for 30 minutes and a solution of t-butyl carbazate (63.09 g, 477 mmol) in toluene (100 mL) was added over a period of 15 minutes. The mixture was heated and stirred at from 70° C. to 75° C. for 1 hour.

The resulting reaction mixture was cooled to 60° C. over a period of 30 minutes, the desired 1,3-dibenzyloxyacetone t-butyloxycarbonylhydrazone (50 mg) was added as seed crystals, and the mixture was stirred at that temperature for 1 hour to grow the crystals. The mixture was cooled to room temperature, stirred overnight and further cooled to 20° C.

Crystals obtained from the obtained suspension by filtration were washed with heptane (300 mL), t-butanol (250 mL), heptane (300 mL) and heptane (300 mL) in this order and dried overnight at 50° C. under reduced pressure and a nitrogen gas stream to obtain the desired 1,3-dibenzyloxyacetone t-butyloxycarbonyl-hydrazone as colorless crystals (120.2 g; yield 85.2% from 1,3-dibenzyloxy-2-propanol).

$^1$H-NMR(270 MHz,CDCl$_3$, δ ppm):9.69(br.s,1H), 7.40–7.25(m,10H), 4.51(s,2H),4.49(s,2H),4.35(s,2H),4.12 (s,2H)

Example 11

Preparation of 1,3-dibenzyloxy-2-t-butyloxycarbonyl-hydrazinopropane hemioxalate

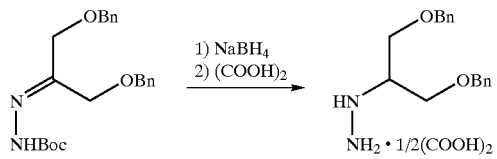

1,3-dibenzyloxyacetone t-butyloxycarbonylhydrazone (10.0 g, 26.0 mmol) was placed in a 200-mL four-necked flask equipped with a magnetic stirrer and a thermometer in a nitrogen atmosphere and suspended in ethanol (80 mL). The mixture was heated to 65° C., a mixture of sodium borohydride (3.44 g, 91.0 mmol) and N,N-dimethylacetamide (57.3 mL) was added over a period of 7 hours or more while maintaining from 65° C. to 68° C., and the mixture was stirred at from 65° C. to 70° C. for 4 hours. The resulting reaction mixture was cooled to room temperature, stirred overnight and further cooled to 0° C. This solution was poured over a period of 50 minutes into 13% aqueous ammonium chloride solution (165 g, 401 mmol) under vigorous stirring cooled to 0° C., while maintaining 5° C. or less. Methyl t-butyl ether (275 mL) was added, the mixture was sufficiently mixed, the resulting two layers were separated, and the obtained organic layer was washed with water (50 mL) four times and 20% saline (50 mL) and dried over anhydrous sodium sulfate. The obtained organic layer (455.1 g) was analyzed by high performance liquid chromatography and as a result it was confirmed that 9.08 g (yield 90%) of 1,3-dibenzyloxy-2-t-butyloxycarbonylhydrazinopropane was formed.

Measurement condition of high performance liquid chromatography:

Column: Zorbax SB-CN

Measurement temperature: 25° C.

Mobile phase: 0.1% pH 7 phosphate buffer solution-acetonitrile (T=0 minute, 50:50 (T=15 minutes, composition of mobile phase: 50:50 (T=25 minutes, composition of mobile phase: 5:95)

Flow rate: 1.0 mL/min

Detection wavelength: 210 nm

The 1,3-dibenzyloxy-2-t-butyloxycarbonylhydrazinopropane-containing solution obtained above was concentrated to dryness, tetrahydrofuran (25 mL) and 6-normal hydrochloric acid (13 mL, 78.0 mmol) were added, and the mixture was heated to 60° C. and stirred for 4 hours. The heating was stopped, and the mixture was allowed to cool to room temperature and stirred overnight. The resulting reaction mixture was added dropwise to deaerated 7% aqueous sodium carbonate solution (123 g, 85.8 mmol) at 5° C. or less. Then deaerated methyl t-butyl ether (300 mL) was added, the mixture was mixed sufficiently and the resulting two layers were separated, the organic layer was washed twice with water (20 mL) and filtered, a small amount of 1,3-dibenzyloxy-2-hydrazinopropane ½ oxalate was added as seed crystals to the obtained filtrate, a solution of oxalic acid (1.17 g, 13.0 mmol) in methanol (13 mL) was added dropwise at room temperature over a period of 1 hour, and the mixture was stirred overnight. Crystals deposited were taken by filtration and washed with methyl t-butyl ether. The crystals were dried overnight under reduced pressure to obtain the desired 1,3-dibenzyloxy-2-hydrazinopropane ½ oxalate (6.57 g) as colorless crystals.

5.92 g of the obtained crystals was taken using a balance and suspended in ethanol (178 mL), and the suspension was deaerated under reduced pressure and made to be under a nitrogen atmosphere. The suspension was heated to 75° C. to give a uniform solution, a small amount of 1,3-dibenzyloxy-2-hydrazinopropane ½ oxalate was added as seed crystals to the solution, while gradually cooling the solution to room temperature, to deposit crystals, and the suspension was stirred overnight at room temperature. The suspension was cooled to 0° C. and stirred for several hours, and the crystals were taken by filtration and washed with ethanol of –10° C. The crystals were dried overnight at room temperature under reduced pressure to obtain the desired 1,3-dibenzyloxy-2-hydrazinopropane ½ oxalate as colorless crystals (5.36 g; yield 68% from the raw material 1,3-dibenzyloxyacetone t-butyloxycarbonylhydrazone).

$^1$H-NMR(270 MHz,DMSO-d$_6$, δ ppm):7.41–7.26(m, 10H),5.91–5.62(br.m, 4H,moved by heavy water addition), 4.50(s,4H),3.56(br.d, J=4.9 Hz,4H),3.34(m,1H)

$^{13}$C-NMR(68 MHz,DMSO-d$_6$, δ ppm):164.7, 138.2, 128.2, 127.5, 127.4, 72.3, 68.3, 59.8

Example 12

Preparation of 1,3-dibenzyloxy-2-t-butyloxycarbonylhydrazinopropane 1,3-dibenzyloxyacetone t-butyloxycarbonylhydrazone (2.00 g, 5.20 mmol) and sodiumborohydride (1.18 g, 31.2 mmol) were placed in a 30-mL egg-plant type flask equipped with a magnetic stirrer and a thermometer in a nitrogen atmosphere, and suspended in ethanol (8 mL). The suspension was heated to 65° C. and stirred for 27 hours. The suspension was cooled to room temperature, stirred overnight and further cooled to 0° C. This solution was poured into 13% aqueous ammonium chloride solution (60 g, 149 mmol) under vigorous stirring cooled to 0° C., while maintaining 5° C. or less. The mixture was extracted with methyl t-butyl ether, the resulting organic layer was washed with water and 20% saline (50 mL) and dried over anhydrous sodium sulfate. The obtained organic layer (128.59 g) was analyzed by high performance liquid chromatography and as a result it was confirmed that 1.91 g (yield 95%) of 1,3-dibenzyloxy-2-t-butyloxycarbonylhydrazinopropane was formed.

Measurement condition of high performance liquid chromatography:

Column: Zorbax SB-CN

Measurement temperature: 25° C.

Mobile phase: 0.1% pH 7 phosphate buffer solution-acetonitrile (T=0 minute, 50:50 (T=15 minutes, composition of mobile phase: 50:50 (T=25 minutes, composition of mobile phase: 5:95)

Flow rate: 1.0 mL/min

Detection wavelength: 220 nm $^1$H-NMR(270 MHz,CDCl$_3$, δ ppm):7.36–7.26(m,10H), 6.05(br.s,1H), 4.54(d,J=12.2 Hz,2H),4.48(d,J=12.2 Hz,2H), 4.54(br.s,1H), 3.59–3.47(m,4H),3.39(m,1H),1.44(s,9H) $^{13}$C-NMR(68 MHz,CDCl$_3$, δ ppm):156.5, 138.1, 128.3, 127.7, 127.6, 80.3, 77.2, 73.2, 69.3, 58.9, 28.3

Example 13

Preparation of 1,3-dibenzyloxy-2-t-butyloxycarbonylhydrazinopropane

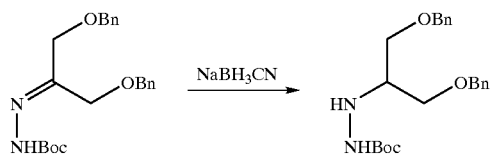

1,3-dibenzyloxyacetone t-butyloxycarbonylhydrazone (2.00 g, 5.20 mmol) and sodium cyanoborohydride (344 mg, 5.20 mmol) were placed in a 50-mL four-necked flask equipped with a magnetic stirrer and a thermometer in a nitrogen atmosphere, and suspended in tetrahydrofuran (10.4 mL). A solution of p-toluenesulfonic acid monohydrate (989 mg, 5.20 mmol) in tetrahydrofuran (5.2 mL) was added to the mixture over a period of 2.5 hours while maintaining 28° C. or less. The mixture was stirred at room temperature for 1 hour and cooled to 0° C., and 1-normal aqueous sodium hydroxide solution (10.4 mL, 10.4 mmol) was added while maintaining 10° C. or less (exothermic heat was recognized). The mixture was extracted with methyl t-butyl ether, and the organic layer obtained was washed with 13% aqueous ammonium chloride solution, water and 20% saline in this order and dried over anhydrous sodium sulfate. The obtained organic layer (131.44 g) was analyzed by high performance liquid chromatography in the same manner as in Example 12 and as a result it was confirmed that 1.76 g (yield 88%) of 1,3-dibenzyloxy-2-t-butyloxycarbonylhydrazinopropane was formed.

Example 14

Preparation of 1,3-dibenzyloxy-2-t-butyloxycarbonylhydrazinopropane

1,3-dibenzyloxyacetone t-butyloxycarbonylhydrazone (2.0 g, 5.20 mmol) and sodium triacetoxyhydroborate (1.83 g, 5.20 mmol) were placed in a 50-mL three-necked flask equipped with a magnetic stirrer and a thermometer in a nitrogen atmosphere, and suspended in tetrahydrofuran (15 mL). A solution of p-toluenesulfonic acid monohydrate (989 mg, 5.20 mmol) in tetrahydrofuran (5 mL) was added to the mixture over a period of 4 hours while maintaining 27° C. or less. The mixture was stirred overnight at room temperature and cooled to 0° C., and 1-normal aqueous sodium hydroxide solution (30.2 mL, 30.2 mmol) was added while maintaining 10° C. or less (exothermic heat was recognized). The mixture was extracted with methyl t-butyl ether, and the organic layer obtained was washed with 13% aqueous ammonium chloride solution, water and 20% saline in this order and dried over anhydrous sodium sulfate. The obtained organic layer (138.66 g) was analyzed by high performance liquid chromatography in the same manner as in Example 12 and as a result it was confirmed that 1.55 g (yield 77%) of 1,3-dibenzyloxy-2-t-butyloxycarbonylhydrazinopropane was formed.

Example 15

Preparation of 1,3-dibenzyloxy-2-t-butyloxycarbonylhydrazinopropane

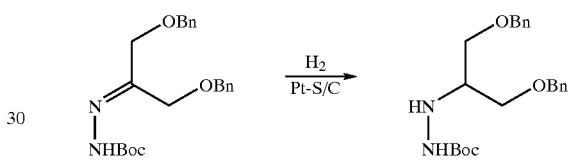

1,3-dibenzyloxyacetone t-butyloxycarbonylhydrazone (500 mg, 1.30 mmol) and 3% Pt-sulfur/carbon powder (423 mg, 0.065 mmol) were suspended in tetrahydrofuran (6.5 mL) in a 30-mL egg-plant type flask equipped with a magnetic stirrer and a thermometer in a nitrogen atmosphere, and the mixture was stirred overnight at room temperature in a hydrogen atmosphere. The inside atmosphere of the flask was replaced with nitrogen, the catalyst was filtered off, and the filtrate was analyzed by high performance liquid chromatography in the same manner as in Example 12 and as a result it was confirmed that 309 mg (yield 61%) of 1,3-dibenzyloxy-2-t-butyloxycarbonylhydrazinopropane was formed.

Example 16

Preparation of 1,3-dibenzyloxy-2-hydrazinopropane hemi-oxalate

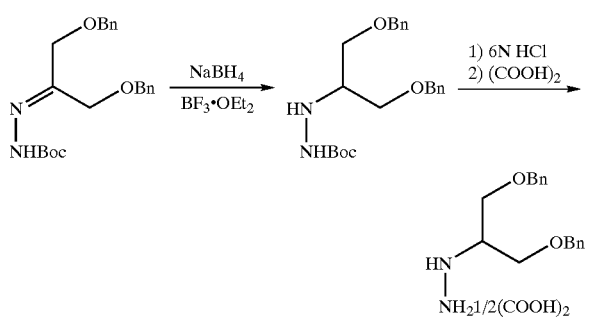

NaBH$_4$ (2.21 g, 58.4 mmol) was placed in a 500-mL four-necked flask and suspended in tetrahydrofuran (40 mL). The suspension was made to be 0° C., a solution of 1,3-dibenzyloxyacetone t-butyloxycarbonylhydrazone (10.0 g, 26.0 mmol) in tetrahydrofuran (30 mL) was gradually added at 10° C. or less, and the vessel was washed with tetrahydrofuran (10 mL). Boron trifluoride diethyl ether complex (4.94 mL, 39.0 mmol) was added portionwise over a period of 15 minutes (10° C. or less) and the mixture was stirred at 1.5–5° C. for 1 hour. 6-normal hydrochloric acid (23.8 mL, 143 mmol) was added portionwise to the resulting reaction mixture over a period of 30 minutes (20° C. or less) and the mixture was stirred at 60–63° C. for 3.5 hours and then at room temperature for 14 hours. The resulting reaction mixture was cooled to 10° C., deaerated 2-normal sodium hydroxide solution (78.0 mL, 156 mmol) was added, the bath was removed, and the mixture was stirred for 10 minutes. The mixture was moved into a separating funnel and extracted with deaerated methyl t-butyl ether (240 mL). The organic layer was washed with water (40 mL), 10% saline (20 mL) and water (40 mL), and the organic layer was made to be 350 mL by addition of methyl t-butyl ether.

10 mg of 1,3-dibenzyloxy-2-hydrazinopropane hemioxalate was added to the organic layer as seed crystals and a solution of oxalic acid (928 mg, 10.3 mmol) in methyl t-butyl ether (10 mL) was added portionwise. The mixture was stirred at room temperature for 30 minutes, a solution of oxalic acid (93 mg, 1.03 mmol) in methyl t-butyl ether (1.0 mL) was added, and the mixture was further stirred at room temperature for 14 hours. The resulting crystals were filtered, washed with methyl t-butyl ether (50 mL) and again washed with methyl t-butyl ether (25 mL) The obtained crystals were dried under reduced pressure to obtain colorless crystals (6.88 g, yield 80%). Physicochemical data of the crystals accorded with those of 1,3-dibenzyloxy-2-hydrazinopropane ½ oxalate obtained in Example 11.

Example 17
Preparation of 1,3-dibenzyloxy-2-hydrazinylpropane hemioxalate

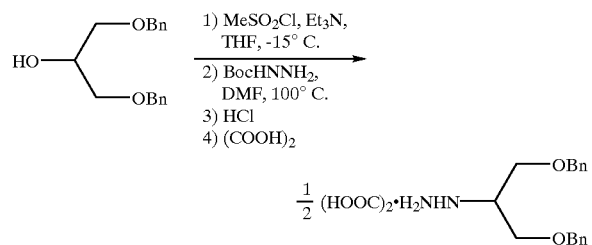

1,3-dibenzyloxy-2-propanol (2.0 g, 7.34 mmol), tetrahydrofuran (19 mL) and triethylamine (3.07 mL, 22.0 mmol) were placed in a 50-mL three-necked flask equipped with a magnetic stirrer and a thermometer under a nitrogen gas stream, and the mixture was cooled to –30° C. Methanesulfonyl chloride (2.27 mL, 29.3 mmol) was added over a period of 10 minutes while maintaining –25° C. or less, and the mixture was stirred at from –30° C. to –25° C. for 30 minutes. The resulting reaction mixture was poured in a mixture of 1-normal hydrochloric acid (11 mL) and methyl t-butyl ether under vigorous stirring cooled to 0° C. The resulting two layers were separated, and the organic layer was washed with 1-normal hydrochloric acid (3.5 mL) (twice), water (3.5 mL) (twice) and 20% saline (7 mL) in this order, dried over anhydrous sodium sulfate, and concentrated under reduced pressure to obtain a light brown oily substance (3.57 g).

The obtained oily substance was moved into a 20-mL egg-plant type flask and dissolved in dimethylformamide (2.75 mL), t-butyl carbazate (6.79 g, 51.4 mmol) was added, and the mixture was heated to 100° C. The mixture was stirred at that temperature for 79 hours, cooled to room temperature and poured in a mixture of water (10 mL) and methyl t-butyl ether under vigorous stirring. The resulting two layers were separated, and the organic layer was washed three times with water and dried over anhydrous sodium sulfate. The obtained organic layer (77.39 g) was analyzed by high performance liquid chromatography in the same manner as in Example 12 and as a result it was confirmed that 1,3-dibenzyloxy-2-t-butyloxycarbonylhydrazinylpropane was formed (893 mg, yield 31%).

The thus obtained solution of 1,3-dibenzyloxy-2-t-butyloxycarbonylhydrazinylpropane was concentrated to dryness, tetrahydrofuran (30 mL) 6-normal hydrochloric acid (9.8 mL, 58.7 mmol) were added, and the mixture was heated to 60° C. and stirred for 3.5 hours. The heating was stopped, the mixture was allowed to cool to room temperature and stirred overnight. The resulting reaction mixture was added dropwise to 10% aqueous sodium carbonate solution (68.5 g, 64.6 mmol). The mixture was extracted with methyl t-butyl ether (100 mL×2), and the organic layers combined were washed twice with 5% saline (20 mL) and dried over anhydrous sodium sulfate.

A solution of oxalic acid (146 mg, 1.62 mmol) in methanol (1.62 mL) was added dropwise to the organic layer at room temperature over a period of 1 hour whereby crystals deposited. The mixture was stirred overnight. The crystals were taken by filtration, washed with methyl t-butyl ether and dried overnight under reduced pressure to obtain the desired 1,3-dibenzyloxy-2-hydrazinylpropane hemioxalate as colorless crystals (544 mg). The obtained crystals were suspended in ethanol (13.6 mL), and the suspension was deaerated under reduced pressure and made to be under a nitrogen atmosphere. The suspension was heated to 75° C. to give a uniform solution, a small amount of 1,3-dibenzyloxy-2-hydrazinylpropane hemioxalate was added to the solution while gradually cooling the solution to room temperature, whereby crystals deposited. The suspension was stirred overnight at room temperature, cooled to 0° C. and stirred for 2 hours, and the crystals were taken by filtration and washed with ethanol of –10° C. The crystals were dried overnight at room temperature under reduced pressure to obtain colorless crystals (474 mg; yield 19% from the raw material 1,3-dibenzyloxy-2-propanol). Physical properties data of the crystals accorded with those of 1,3-dibenzyloxy-2-hydrazinylpropane hemioxalate obtained in Example 11.

INDUSTRIAL APPLICABILITY

By the preparation process of the invention, the compound useful as a cancer-treating agent in the medicinal field can be prepared safely and easily.

What is claimed is:

1. A process for preparation of an indolopyrrolocarbazole derivative represented by the formula [I]

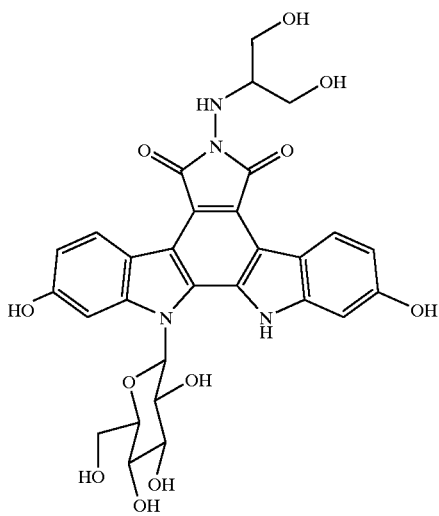

which comprises (1) treating a compound represented by the general formula [V]:

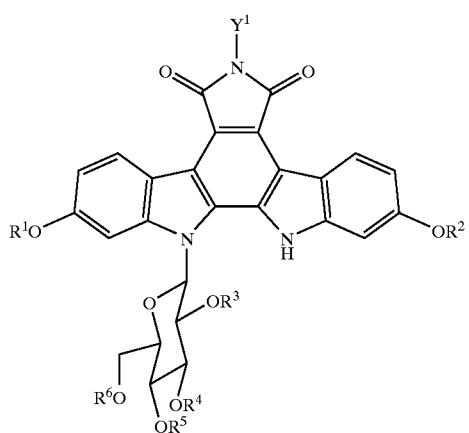

wherein, $Y^1$ represents a hydrogen atom, an alkyl group having 1 to 4 carbon atoms, a phenyl group, a benzyloxymethyl group or an aralkyl group, and $R^1$, $R^2$, $R^3$, $R^4$, $R^5$ and $R^6$ may be the same or different and each represent a protective group of a hydroxyl group, with a base in an inert solvent to obtain a compound represented by the general formula [IV]:

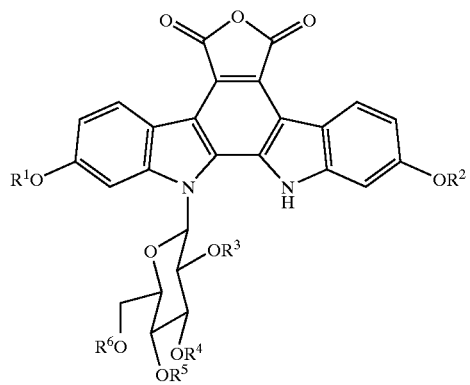

wherein, $R^1$, $R^2$, $R^3$, $R^4$, $R^5$ and $R^6$ may be the same or different and each represent a protective group of a hydroxyl group;

(2) reacting the compound represented by the general formula [IV] with a hydrazinediol derivative acid addition salt represented by the general formula [III]:

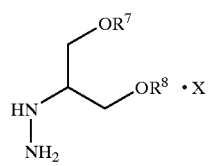

wherein, X represents an acid molecule, and $R^7$ and $R^8$ may be the same or different and each represent a hydrogen atom or a protective group of a hydroxyl group, in the presence of an acid-capturing agent to obtain a compound represented by the general formula [II]:

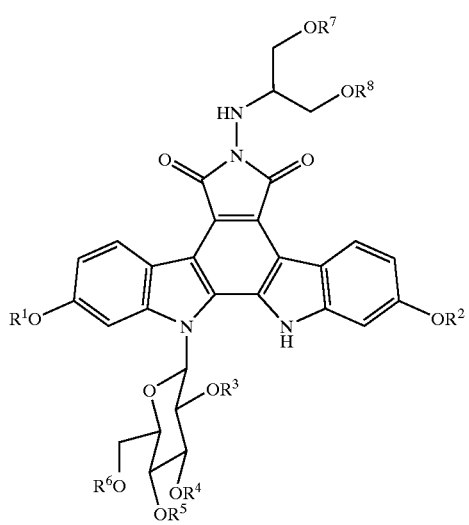

wherein, $R^1$, $R^2$, $R^3$, $R^4$, $R^5$ and $R^6$ may be the same or different and each represent a protective group of a hydroxyl group, and $R^7$ and $R^8$ may be the same or different and each represent a hydrogen atom or a protective group of a hydroxyl group; and (3) removing the protective groups of the compound represented by the general formula [II].

2. The process according to claim 1 wherein $R^1$, $R^2$, $R^3$, $R^4$, $R^5$, $R^6$, $R^7$ and $R^8$ are benzyl groups.

3. The process according to claim 1 wherein $R^1$, $R^2$, $R^3$, $R^4$, $R^5$ and $R^6$ are benzyl groups and $R^7$ and $R^8$ are hydrogen atoms.

4. The process according to claim 1 wherein X is oxalic acid.

5. The process according to claim 1 wherein $Y^1$ is a methyl group.

6. A compound represented by the general formula [IV]:

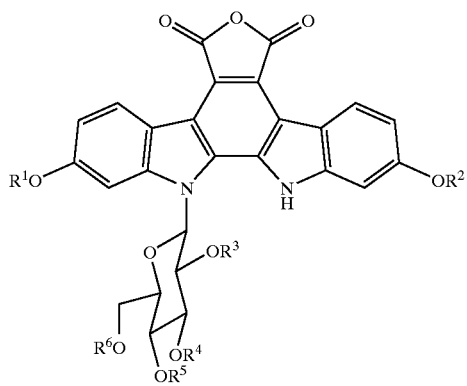

[IV]

wherein, $R^1$, $R^2$, $R^3$, $R^4$, $R^5$ and $R^6$ may be the same or different and each represent a protective group of a hydroxyl group.

7. The compound according to claim 6 wherein $R^1$, $R^2$, $R^3$, $R^4$, $R^5$ and $R^6$ are benzyl groups.

8. A compound represented by the general formula [II]:

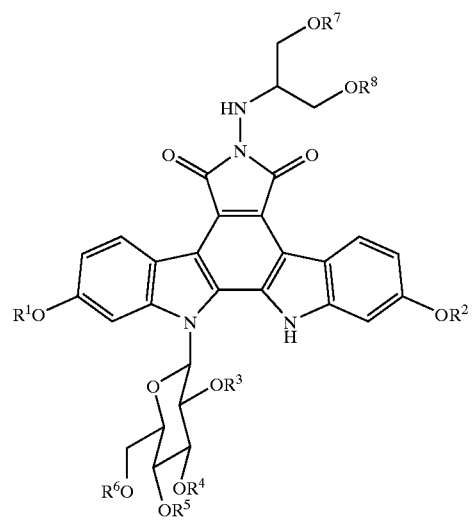

[II]

wherein, $R^1$, $R^2$, $R^3$, $R^4$, $R^5$ and $R^6$ may be the same or different and each represent a protective group of a hydroxyl group, and $R^7$ and $R^8$ may be the same or different and each represent a hydrogen atom or a protective group of a hydroxyl group.

9. The compound according to claim 8 wherein $R^1$, $R^2$, $R^3$, $R^4$, $R^5$, $R^6$, $R^7$ and $R^8$ are benzyl groups.

10. The compound according to claim 8 wherein $R^1$, $R^2$, $R^3$, $R^4$, $R^5$ and $R^6$ are benzyl groups, and $R^7$ and $R^8$ are hydrogen atoms.

11. A hydrazinediol derivative acid addition salt represented by the general formula [III]:

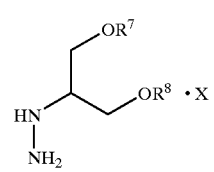

[III]

wherein, X represents an acid molecule, and $R^7$ and $R^8$ may be the same or different and each represent a hydrogen atom or a protective group of a hydroxyl group.

12. The compound according to claim 11 wherein $R^7$ and $R^8$ are benzyl groups.

13. The compound according to claim 11 wherein $R^7$ and $R^8$ are hydrogen atoms.

14. The compound according to claim 11 wherein X is oxalic acid.

15. A process for preparation of a hydrazinediol derivative acid addition salt represented by the general formula [III']:

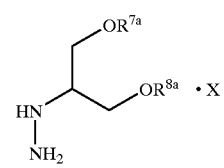

[III']

wherein, $R^{7a}$ and $R^{8a}$ may be the same or different and each represent a protective group of a hydroxyl group, and X represents an acid molecule, which comprises reacting a hydrazinediol derivative represented by the general formula [III-a]:

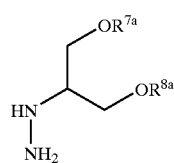

[III-a]

wherein, $R^{7a}$ and $R^{8a}$ are as defined above, with an acid.

16. The process according to claim 15 wherein $R^{7a}$ and $R^{8a}$ are benzyl groups.

17. The process according to claim 15 wherein the hydrazinediol derivative represented by the general formula [III-a] is obtained by eliminating the protective group of the amino group of a hydrazinediol derivative represented by the general formula [III-b]:

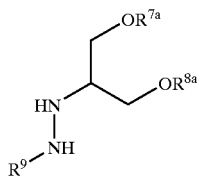

wherein R$^{7a}$ and R$^{8a}$ each represent a protective group of a hydroxyl group and R$^9$ represents a protective group of an amino group.

18. The process according to claim 17 wherein R$^{7a}$ and R$^{8a}$ are benzyl groups and R$^9$ is a t-butoxycarbonyl group.

19. The process according to claim 17 wherein the hydrazinediol derivative represented by the general formula [III-b] is obtained by reducing a hydrazone derivative represented by the general formula [III-c]:

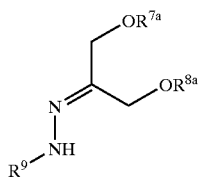

wherein R$^{7a}$ and R$^{8a}$ may be the same or different and each represent a protective group of a hydroxyl group, and R$^9$ represents a protective group of an amino group.

20. The process according to claim 19 wherein R$^{7a}$ and R$^{8a}$ are benzyl groups and R$^9$ is a t-butoxycarbonyl group.

21. The process according to claim 19 wherein the hydrazone derivative represented by the general formula [III-c] is obtained by reacting a dihydroxyacetone derivative represented by the general formula [III-e]:

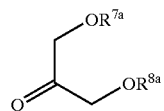

wherein R$^{7a}$ and R$^{8a}$ each represent a protective group of a hydroxyl group, with a hydrazine derivative represented by the general formula [III-d]:

wherein R$_9$ is a protective group of an amino group,
in a mixed solvent.

22. The process according to claim 21 wherein R$^{7a}$ and R$^{8a}$ are benzyl groups and R$^9$ is a t-butoxycarbonyl group.

23. The process according to claim 21 wherein the dihydroxyacetone derivative represented by the general formula [III-e] is obtained by reacting a propanetriol derivative represented by the general formula [III-f]:

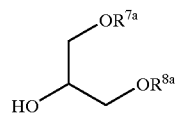

wherein R$^{7a}$ and R$^{8a}$ may be the same or different and each represent a protective group of a hydroxyl group, with a hypochlorite in an inert solvent in the presence of a catalyst and a buffer.

24. The process according to claim 23 wherein R$^{7a}$ and R$^{8a}$ are benzyl groups and R$^9$ is a t-butoxycarbonyl group.

25. A hydrazinediol derivative represented by the general formula [III-a]:

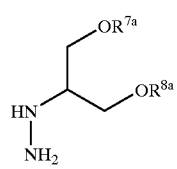

wherein, R$^{7a}$ and R$^{8a}$ may be the same or different and each represent a protective group of a hydroxyl group.

26. The compound according to claim 25 wherein R$^{7a}$ and R$^{8a}$ are benzyl groups.

27. A hydrazinediol derivative represented by the general formula [III-b]:

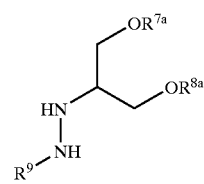

wherein R$^{7a}$ and R$^{8a}$ each represent a protective group of a hydroxyl group and R represents a protective group of an amino group,
or a salt thereof.

28. The compound according to claim 27 wherein R$^{7a}$ and R$^{8a}$ are benzyl groups and R$^9$ is a t-butoxycarbonyl group.

29. A hydrazone derivative represented by the general formula [III-c]:

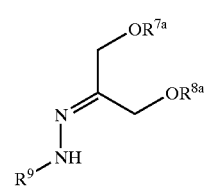

wherein R$^{7a}$ and R$^{8a}$ may be the same or different and each represent a protective group of a hydroxyl group, and R$^9$ represents a protective group of an amino group.

30. The compound according to claim 17 wherein R$^{7a}$ and R$^{8a}$ are benzyl groups and R$^9$ is a t-butoxycarbonyl group.

31. The process according to claim 17 wherein the hydrazinediol derivative represented by the general formula [III-b] is obtained by reacting a propanediol derivative represented by the general formula [III-g]:

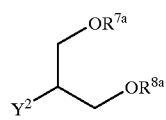
[III-g]
wherein $R^{7a}$ and $R^{8a}$ may be the same or different and each represent a protective group of a hydroxyl group, and $Y^2$ represents an eliminable group,
with a hydrazine derivative represented by the general formula [III-d]:
[III-d]
wherein $R^9$ represents a protective group of an amino group,
in an inert solvent.
* * * * *